US008507266B2

(12) United States Patent
Welter et al.

(10) Patent No.: US 8,507,266 B2
(45) Date of Patent: Aug. 13, 2013

(54) APPARATUS AND METHOD FOR TISSUE ENGINEERING

(75) Inventors: Jean F. Welter, Shaker Heights, OH (US); Luis A. Solchaga, University Heights, OH (US); Jim A. Berilla, Highland Heights, OH (US); Kitsie Penick, Austinburg, OH (US)

(73) Assignee: Case Western Reserve University, Cleveland, OH (US)

( * ) Notice: Subject to any disclaimer, the term of this patent is extended or adjusted under 35 U.S.C. 154(b) by 950 days.

(21) Appl. No.: 10/578,212

(22) PCT Filed: Nov. 4, 2004

(86) PCT No.: PCT/US2004/036893
§ 371 (c)(1),
(2), (4) Date: May 4, 2006

(87) PCT Pub. No.: WO2005/047466
PCT Pub. Date: May 26, 2005

(65) Prior Publication Data
US 2007/0042490 A1    Feb. 22, 2007

Related U.S. Application Data

(60) Provisional application No. 60/517,270, filed on Nov. 4, 2003.

(51) Int. Cl.
*C12M 1/22* (2006.01)
*C12M 3/00* (2006.01)

(52) U.S. Cl.
USPC .................. 435/305.2; 435/289.1; 435/298.1; 435/304.1; 435/305.1; 435/303.1

(58) Field of Classification Search
USPC .......... 435/289.1, 298.1, 304.1, 305.1, 303.1, 435/305.2
See application file for complete search history.

(56) References Cited

U.S. PATENT DOCUMENTS

| | | | |
|---|---|---|---|
| 4,225,671 A * | 9/1980 | Puchinger et al. | 435/70.3 |
| 5,416,022 A | 5/1995 | Amiot | |
| 5,686,304 A | 11/1997 | Codner | |
| 5,985,653 A | 11/1999 | Armstrong et al. | |
| 5,994,129 A | 11/1999 | Armstrong et al. | |
| 6,008,049 A | 12/1999 | Naughton et al. | |
| 6,048,721 A | 4/2000 | Armstrong et al. | |
| 6,121,042 A | 9/2000 | Peterson et al. | |
| 6,197,575 B1 | 3/2001 | Griffith et al. | |
| 6,207,448 B1 | 3/2001 | Rozga et al. | |
| 6,228,635 B1 | 5/2001 | Armstrong et al. | |
| 6,238,908 B1 | 5/2001 | Armstrong et al. | |
| 6,468,792 B1 | 10/2002 | Bader | |
| 6,479,252 B1 | 11/2002 | Barbera-Guillem et al. | |
| 6,562,616 B1 | 5/2003 | Toner et al. | |
| 6,607,910 B1 | 8/2003 | Dimitrijevich et al. | |
| 2003/0008388 A1 | 1/2003 | Barbera-Guillem et al. | |
| 2004/0077075 A1* | 4/2004 | Jensen et al. | 435/297.2 |
| 2004/0132175 A1* | 7/2004 | Vetillard et al. | 435/297.1 |

FOREIGN PATENT DOCUMENTS
WO    WO-02/06441 A1 *   1/2002

* cited by examiner

*Primary Examiner* — Nathan Bowers
(74) *Attorney, Agent, or Firm* — Tarolli, Sundheim, Covell & Tummino LLP

(57) ABSTRACT

A bioreactor system includes a housing and a hydrostatic loading module. The housing includes a chamber with an inlet port and an outlet port. The inlet and outlet ports allowing the chamber to be continuously perfused with a culture medium while chamber is hydrostatically loaded.

44 Claims, 22 Drawing Sheets

APPARATUS AND METHOD FOR TISSUE ENGINEERING

RELATED APPLICATION

The present application claims priority from U.S. Provisional Patent Application Ser. No. 60/517,270, filed Nov. 4, 2003 which is herein incorporated by reference in its entirety.

TECHNICAL FIELD

The present invention relates generally to apparatuses and methods for tissue engineering, and more particularly, to apparatuses and methods for generating tissue-engineered constructs.

BACKGROUND OF THE INVENTION

The culturing of living cells in vitro is performed for a variety of purposes, including the preparation of viral vaccines, the recovery of by-products of cell metabolism, and the production of tissue or tissue-like derivatives for creating implants or artificial organs. Cell types that can be grown in culture can include connective tissue cells, skeletal cells, cardiac cells, epithelial cells, neural cells, endocrine cells, melanocytes, and many types of tumor cells. A variety of media are available, depending on the particular growth requirements of the cells and the growth conditions.

Typically, cell culture production of either cells or cell-secreted products begins with the small scale growth of cells. Traditional vessels for small volume cultures include multi-well plates, T-flasks, roller bottles and spinner flasks. In recent years a number of manufacturers have also begun to offer cell culture devices in the form of flexible, disposable bags formed of biologically inert and gas-permeable plastic materials such as fluoro-ethylene-propylene copolymers. Cell culture devices that involve the use of oxygen-permeable materials have also been used in recent years. For instance, a cell culture device can be constructed from a petri-dish that includes a base, which consists of a gas-permeable membrane, such as silicone rubber. Alternatively, a cell culture device can be constructed from a Roux bottle in which a side wall comprises the gas-permeable membrane.

Several problems are associated with growing cells in vitro to produce dense masses of cells. First, individual components of the nutrient medium must diffuse through the cell layers to reach all cells. This becomes increasingly difficult as the thickness of the cell layer increases. Second, the maintenance of a suitable environment for cell growth is difficult because the fluid immediately adjacent a growing cell is continuously changing as cellular metabolism proceeds and is returned to its original status only in stepwise fashion when the nutrient medium is changed or agitated en masse. Third, a lattice or suitable material upon which to grow some types of cells is often required.

SUMMARY OF THE INVENTION

The present invention relates to apparatuses and methods for tissue engineering. More particularly, the present invention relates to apparatuses and methods for generating tissue-engineered constructs, such as tissue-engineered cartilage implants for articular cartilage repair. It will be appreciated by one skilled in the art that the apparatuses and methods of the present invention can be used for generating other cell or tissue constructs, such as tissue-engineered skin, tissue-engineered bone, and tissue-engineered tendon.

In accordance with one aspect of the invention, cells and/or tissue-engineered constructs can be grown in a bioreactor system that can provide continuous perfusion of a culture or growth medium (e.g., chondrogenic medium) to help improve mass transfer rates of cells of the tissue-engineered constructs. The bioreactor system can provide multiple stimuli to the cells simultaneously, and can be instrumented for diagnostic measurements. The bioreactor system can be modular and comprise a housing defining a bioreactor chamber that contains a culture or growth medium. The housing includes an inlet port and an outlet port for fluid flow through the bioreactor chamber. At least one gas permeable membrane defines at least a portion of the housing. The membrane allows gas flow through the housing into the chamber. A hydrostatic loading module can transmit hydrostatic pressure through the membrane to the culture or growth medium contained in the chamber.

The bioreactor system can be designed as a self-contained system, which, after being assembled in a sterile environment, does not need to be opened until the end of the run. The chamber can be perfused with culture or growth medium using a microprocessor controlled pump. The medium can be collected in waste containers and not recycled. The flow-through approach avoids intermittent drastic changes in the extracellular environment associated with bulk medium exchanges, and can allow the establishment of a stable extracellular environment.

A further aspect of the invention relates to a method of improving survival of a tissue-engineered implant formed using adult mesenchymal stem cells. In the method, a suspension of mesenchymal stem cells can be placed in a culture medium contained in a sterile conical-bottomed vessel (e.g., polypropylene vessel). A plurality of cells (e.g., about 200,000 to about 250,000 cells) can be placed in the vessel, and these cells can then be centrifuged to aggregate (i.e., pellet) the cells. The resulting aggregates can be maintained in culture for several days to allow chondrogenesis to begin. After remaining in culture for several days, the cultured cells can be released from the aggregate environment by enzymatic digestion, and can then be used to seed large-scale tissue-engineered constructs (e.g., implants). Use of this method provides: markedly enhanced viability throughout the tissue-engineered implants; chondrogenic differentiation of cells from mesenchymal stem cell preps that otherwise exhibited poor chondrogenic potential; and abundant chondroid extracellular matrix production.

Another aspect of the present invention relates to a pre-treatment regimen to improve chondrogenesis by adult-bone marrow derived mesenchymal progenitor cells. In the method, bone marrow derived mesenchymal stem cells can be isolated from bone marrow biopsies. The cells can then be expanded in culture using a standardized set of culture conditions. Human recombinant fibroblast growth factor 2 (rhFGF-2) can be added to the human bone marrow derived mesenchymal stem cell culture at the first medium change (e.g., on days 3 or 4) following isolation from the bone marrow biopsy, and throughout the entire monolayer culture expansion phase. The rhFGF-2 can be added to culture medium, for example, at about 1 to about 10 ng/ml final concentration, and the culture medium can be changed, for example, about two times per week. The cells can be passaged just prior to confluence. Use of this method provides marked enhancement (e.g., about 2 to about 3 fold) of the proliferation rate of the cells in monolayer culture, markedly enhanced expression of markers of chondrogenesis by rhFGF-2 pre-treated mesenchymal stem cells exposed to the appropriate stimuli, and rescue of mesenchymal stem cell preparations that displayed poor chondrogenic potential.

Yet another aspect of the present invention relates to a treatment regimen to improve chondrogenesis by adult-bone marrow derived mesenchymal progenitor cells. In the method, bone marrow derived mesenchymal stem cells can be isolated from bone marrow biopsies. The cells can then be expanded in culture using a standardized set of culture conditions. The expanded cells can then be seeded onto constructs (e.g., biocompatible scaffolds). The assembled constructs can be grown in a continuous perfusion bioreactor with a chondrogenic medium that includes dexamethasone (e.g., $10^{-7}$ M). The dexamethasone concentration can be reduced in order to induce the internal synthesis of BMP-2, a chondrogenic growth factor.

BRIEF DESCRIPTION OF THE DRAWINGS

Further features of the present invention will become apparent to those skilled in the art to which the present invention relates from reading the following description of the invention with reference to the accompanying drawings in which.

DETAILED DESCRIPTION

The present invention relates to apparatuses and methods for tissue engineering, and, particularly, to apparatuses and methods for generating tissue-engineered constructs, such as tissue-engineered cartilage implants for articular cartilage repair. One apparatus in accordance with the present invention comprises a bioreactor system. The bioreactor system allows continuous perfusion of, for example, nutrients, growth factors and waste products, to and from cells or tissues cultured or grown in the bioreactor system. The bioreactor system in accordance with invention is designed to provide multiple stimuli to the cells simultaneously, as well as be instrumented for diagnostic measurements. For example, the bioreactor system can include monitoring instrumentation and mechanical stimulation modules to monitor or affect environmental parameters, such as pH, temperature, solute concentrations, and oxygenation. The monitoring instrumentation can be set up to clamp selected environmental parameters at specific predetermined values, while allowing others to float as outcome variables. The monitoring information can be set to flag specific conditions as requiring intervention, which is useful for a clinical setting, where maintaining a sterile environment is critical. The bioreactor system in accordance with the present invention provides a self-contained system, which, after being assembled in a sterile environment, does not need to be opened until the end of the operation.

Figure 1:
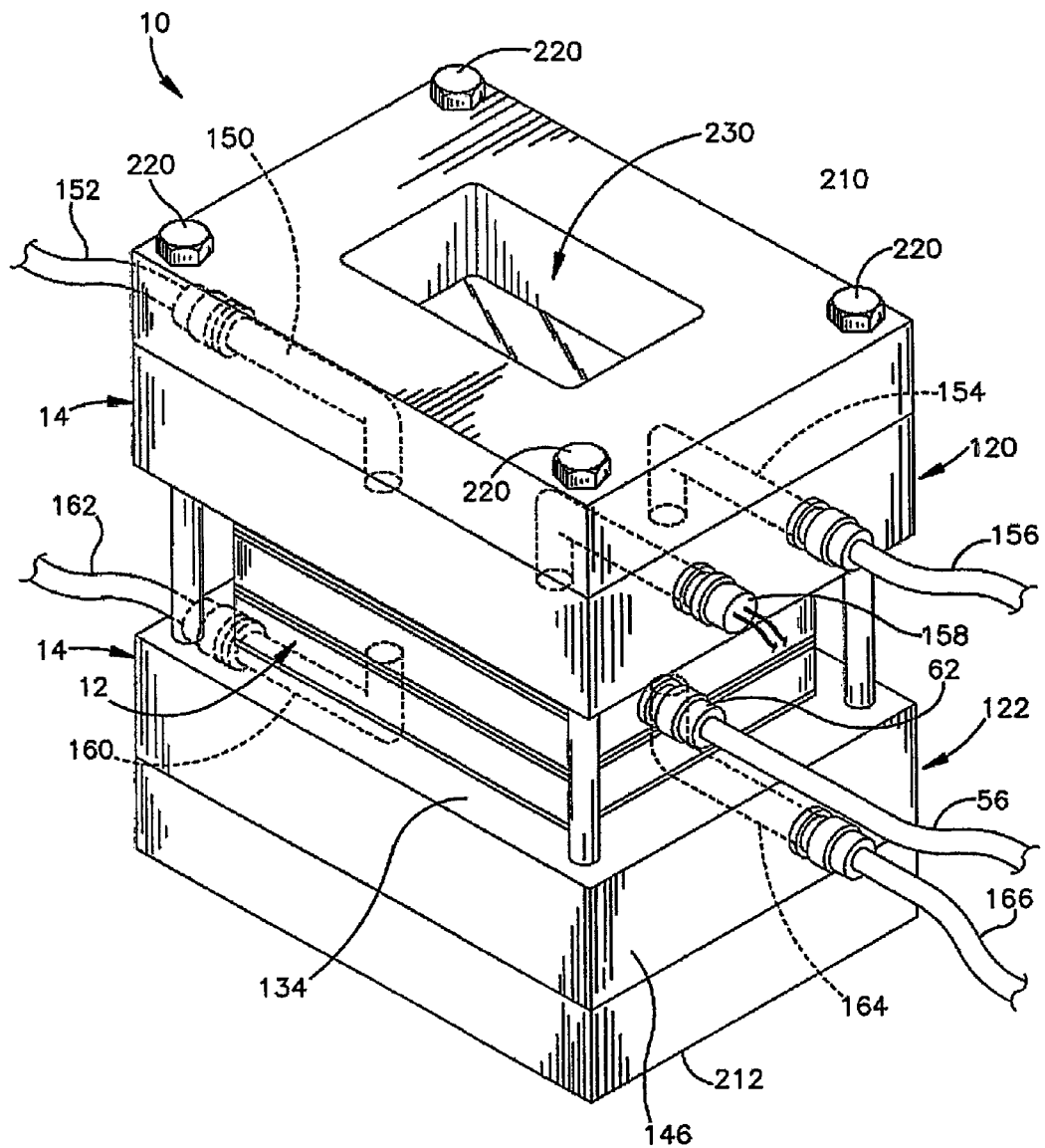
FIG. 1 illustrates a schematic perspective view of a bioreactor system in accordance with an aspect of the present invention.
Figure 2:
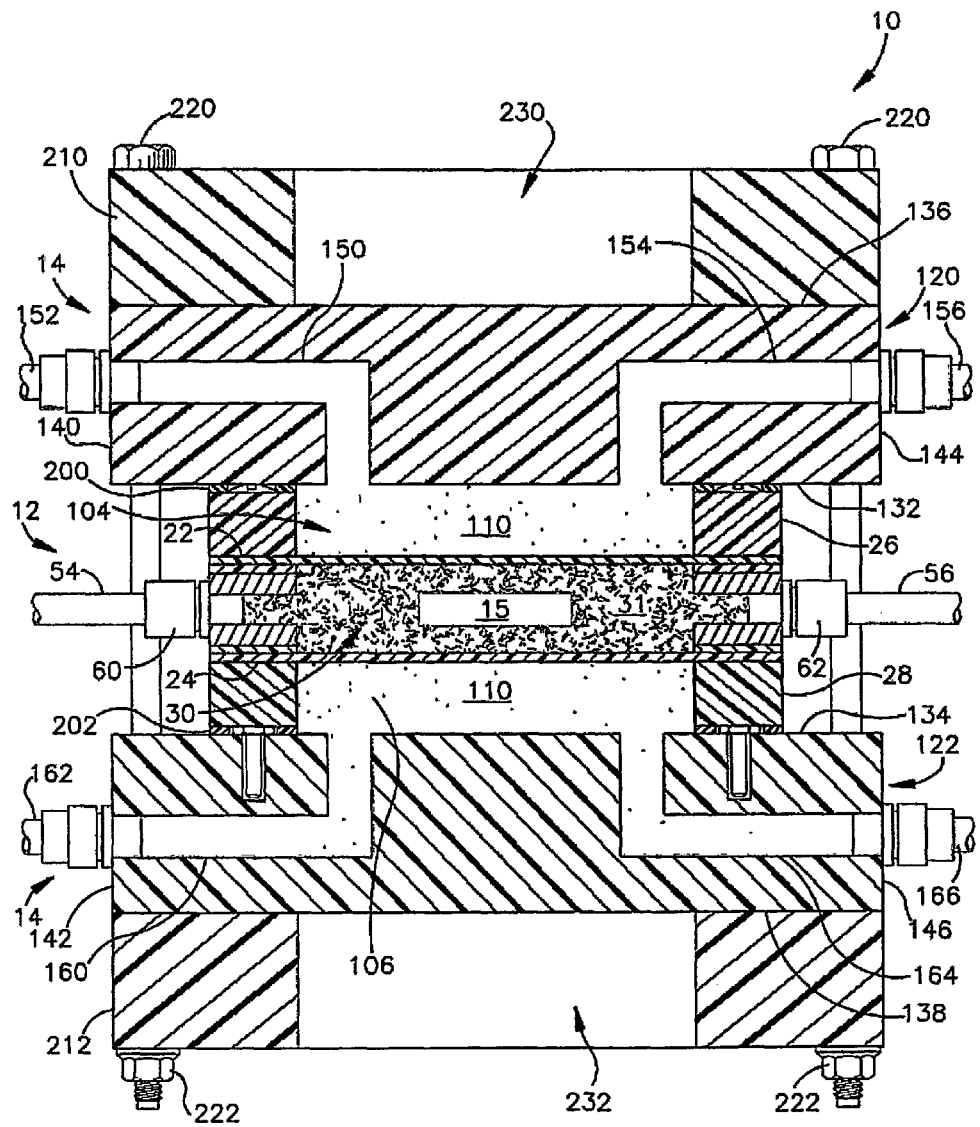
FIG. 2 illustrates a schematic cross-sectional view of the bioreactor system of FIG. 1.

FIGS. 1 and 2 illustrate a bioreactor system 10 in accordance with an aspect of the invention. The bioreactor system 10 includes a bioreactor housing 12 and a hydrostatic loading module 14 that is coupled to the bioreactor housing 12. The bioreactor housing 12 can be used for culturing or growing tissue or cells 15 (FIG. 2), such as stem cells (e.g., mesenchymal stem cells and hematopoietic stem cells as well as differentiated or specialized cells (e.g., chondrocytes, muscle cells or neural cells). The hydrostatic loading module 14 transmits hydrostatic pressure to the cells or tissue 15 cultured or grown in the bioreactor housing 12 without removing the cells or tissue 15 or otherwise breaching the bioreactor housing 12. This is desirable for cells or tissue 15 destined for implantation in patients.

Figures 3, 4:
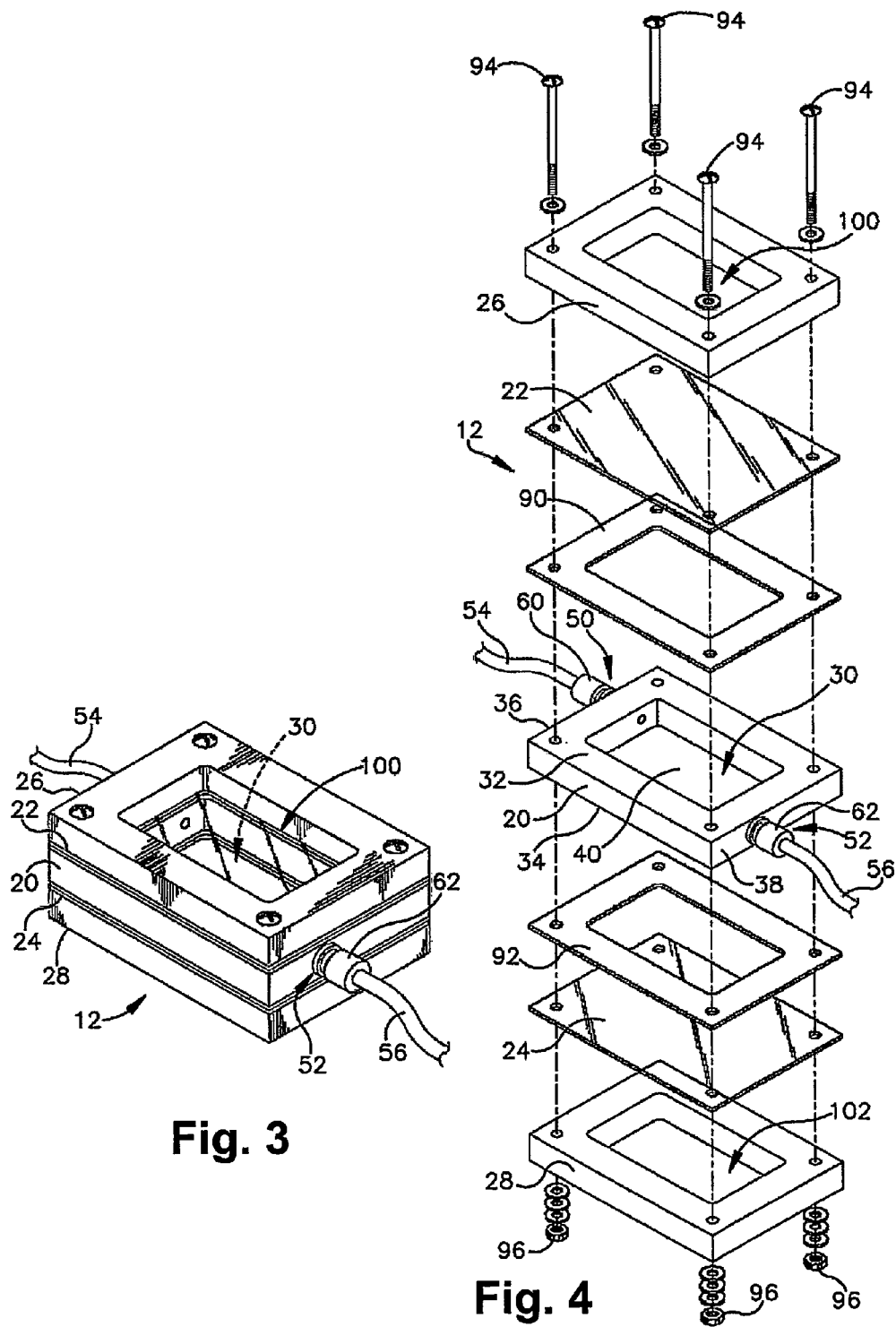
FIG. 3 illustrates a schematic perspective view of a bioreactor housing of the bioreactor system in accordance with an aspect of the invention.
FIG. 4 illustrates an expanded schematic perspective view of the bioreactor housing of the bioreactor system in accordance with an aspect of the invention.

Referring to FIGS. 3 and 4, the bioreactor housing 12 is modular and comprises an inner frame 20 that is sandwiched between a first membrane 22 and a second membrane 24. The first membrane 22 and the second membrane 24 are sandwiched between a first outer frame 26 and a second outer frame 28. The inner frame 20 can be formed from a biocompatible composition, such as a plastic, thermoplastic, synthetic, or natural material, which can be fabricated into a substantially rigid framework structure. The framework structure has a structural integrity to withstand loading in the MPa range. It will be apparent to those skilled in the art that a wide variety of materials for formation and/or fabrication of the inner frame 20 can also be used.

The inner frame 20 is substantially annular in shape and defines a bioreactor culture or growth chamber 30. The bioreactor chamber 30 forms the core of the bioreactor system 10. The bioreactor chamber 30 can have a chamber volume that can contain a first liquid medium 31 (FIG. 2), such as a culture medium or growth medium, and cells or tissue 15 cultured in the first liquid medium. The first liquid medium can be a liquid solution that can be used to provide sufficient nutrients (e.g., vitamins, amino acids, essential nutrients, salts, and the like) and properties (e.g., osmolarity, buffering) to maintain living cells (or living cells in a tissue) and support their growth. The first liquid medium may include one or more of tissue culture medium alone, tissue culture medium with cells, physiological buffers, and/or a drug or cytokine or growth factor or enzyme (e.g., solution of trypsin) or other biological agent to treat cells cultured therein. Commercially available cell and tissue culture medium is known to those skilled in the art.

The dimensions of the inner frame 20 can depend on one or more factors including, but not limited to, the desired fluid capacity of the bioreactor chamber 30 formed therewith, and the dimensions of the bioreactor chamber 30. In one aspect of the invention, the inner frame 20 can be substantially rectangular in shape, and comprise a first substantially planar surface 32 and a second substantially planar surface 34 that is spaced apart and aligned with the first substantially planar surface 32. The first surface 32 and the second surface 34 extend substantially parallel between a first end 36 and a laterally spaced second end 38. A substantially rectangular opening 40, which defines the dimensions of the bioreactor chamber 30, extends between the first surface 32 and the second surface 34. It will be appreciated by one skilled in the art that the inner frame 20 can have a length, width, and height, which defines a bioreactor chamber 30 for culturing or growing of cells or tissue in less incubator space than would be required for culturing or growing of cells or tissue at a comparable growth rate or to a comparable cell density using a conventional cell culture apparatus.

Figure 5:
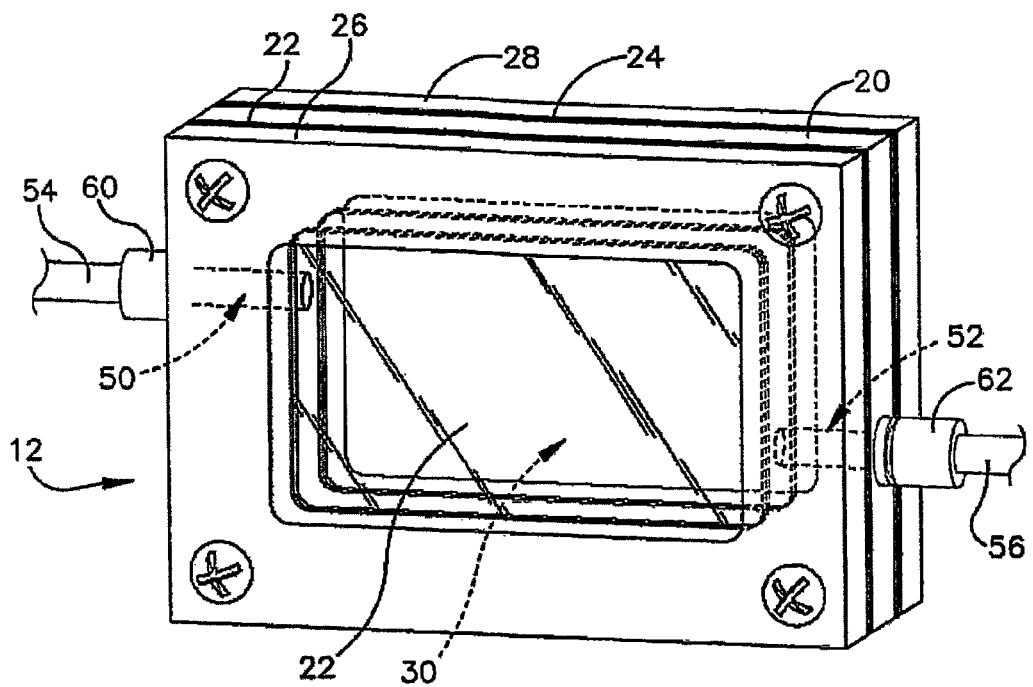
FIG. 5 illustrates a schematic perspective view of a bioreactor housing of the bioreactor system in accordance with another aspect of the invention.

Referring to FIGS. 2 and 5, the inner frame 20 includes at least one inlet port 50 and outlet port 52 that are provided respectively at the first end 36 and the second end 38 of the inner frame 20. The inlet port 50 is coupled to a fluid feed line or conduit 54, and the outlet port 52 is coupled to the fluid exhaust line or conduit 56. The inlet port 50 and the outlet port 52 can serve as a passageway through which the first liquid medium 31 is introduced and withdrawn from the bioreactor chamber 30. A computer controlled syringe pump (not shown) can control perfusion of the first liquid medium 31 through the inlet port 50 and the outlet port 52. The first liquid medium 52 perfused through the bioreactor chamber 30 can pass though the exhaust line 56, be collected in waste containers, and not recycled. This flow-through approach avoids intermittent drastic changes in the extracellular environment associated with bulk medium exchanges and allows the establishment of a stable extracellular environment in the bioreactor chamber 30.

The flow of the first liquid medium 31 through inlet port 50 and the outlet port 52 is regulated with a first medium control valve 60 and a second medium control valve 62. The medium control valves 60 and 62 can be at least partially opened or closed to adjust the flow rate of the first liquid medium 31 through the bioreactor chamber 30 as well as to seal the bioreactor chamber 30 during hydrostatic loading (i.e., increases in the hydrostatic pressure) of the bioreactor chamber 31 by the hydrostatic loading module 14. Sealing of the bioreactor chamber 30 during hydrostatic loading allows the hydrostatic pressure of bioreactor chamber 30 to be increased without loss of first liquid medium from the bioreactor chamber 30.

By way of example, the medium control valves 60 and 62 can comprise electromagnetic (magnetic type 15-5PH stainless steel) needle valves, which allow computer control of the medium flow through the bioreactor chamber 30. One example of an electromagnetic valve (not shown) utilizes an electromagnetic coil and housing with a valve seat, a valve, and spring assembly. In operation, when the bioreactor chamber is pressurized, pressure inside the bioreactor chamber 30, assisted by spring-loading of the electromagnetic valve, seals off the medium flow.

Depending on factors such as the amount of the first liquid medium 31 introduced into the bioreactor chamber 30, and the size of the inlet port 50 and the outlet port 52, it may sometimes be necessary to provide venting of the bioreactor chamber 30. Venting is a process in which air or gas can be displaced from the bioreactor chamber when the first liquid medium 31 is introduced into the bioreactor chamber 30. Venting may be necessary to relieve pressure on the membranes of the cell culture chamber caused by the injection of air during the process of introducing the first liquid medium 31 into the bioreactor chamber 30.

The inlet port 50 and the outlet port 52 can be resealable by a suitable means known in the art such as a cap, a plug, or other suitable means, for example, after culturing or growing cells or tissue in the bioreactor chamber 30. By way of example, the inlet and outlet ports 50 and 52 can be substantially filled and sealed with a material comprising gasket that is sufficiently pliable to be self-sealing, thereby allowing for penetration by a needle and resealing after needle withdrawal. Such material is known to those skilled in the art, and may include, but is not limited to one or more of rubber, silicone, silicone-rubber, or other elastomeric material suitable for the intended purpose.

Figure 6:
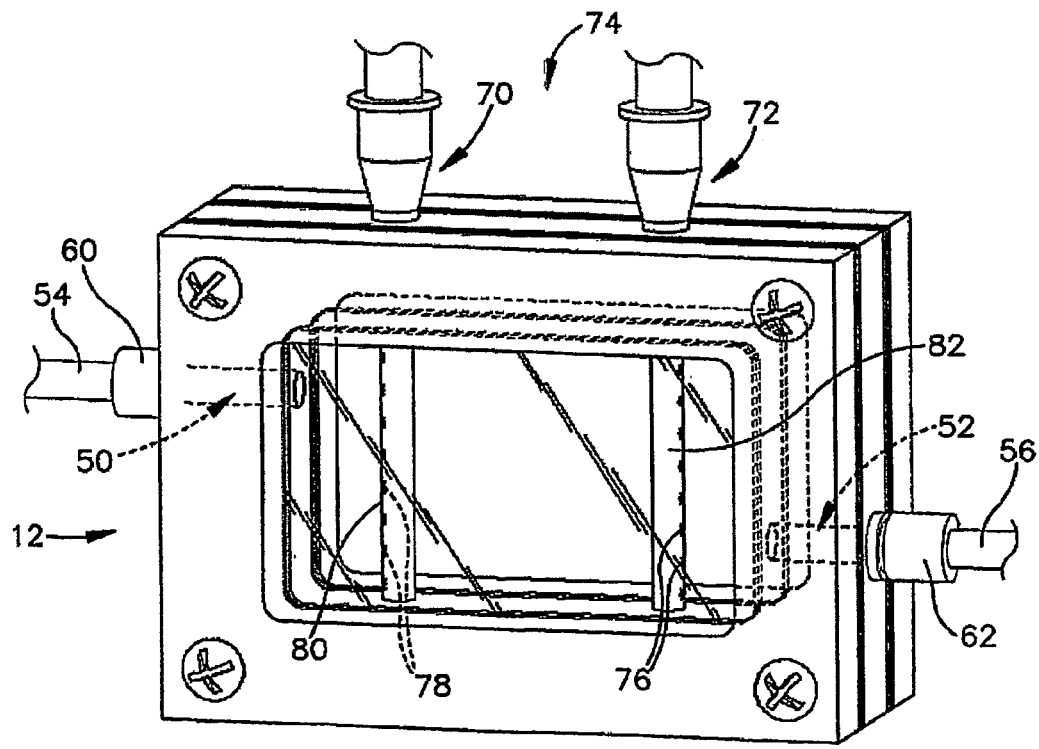
FIG. 6 illustrates a schematic perspective view of a bioreactor housing with an internal mixing circuit in accordance with yet another aspect of the invention.

The inner frame 20 can also include additional ports for instrumentation, sample collection, and media recirculation. For example, FIG. 6 illustrates that additional ports 70 and 72 are provided for an internal mixing device 74, which circulates the first liquid medium 31 independent of the medium replenishment rate provided through the inlet and outlet ports 50 and 52. This allows changes in hydrodynamics inside the bioreactor chamber 30 without increasing medium usage.

By way of example, the internal mixing device can include a magnetically driven impeller (not shown) that recirculates the first liquid medium 31 through a first series of channels 76 and second series of channels 78 that are provide in the bioreactor chamber 30. The first series of channels 76 and the second series of channels are provided on respectively a first member 80 and a second member 82 that situated at opposite ends of the bioreactor chamber 30. The rotational speed of the impeller can be controlled by an external solid-state magnetic driver. The internal mixing device 74 can provide a recirculation rate of, for example, at least one bioreactor chamber volume per minute. It will be appreciated by one skilled the art that mathematical modeling techniques can be used to optimize the flow rates used in the internal mixing methodology for maximum mass transport and minimum shear stress.

Referring again to FIG. 3, the first membrane 22 and second membrane 24 can comprise gas permeable membranes. By "gas permeable" in accordance with the invention, it is meant that the membranes 22 and 24 are liquid impermeable, allow transfer of gases, and are capable of excluding microbial contamination (e.g., pore size is sufficiently small enough to exclude passage of microbes commonly encountered in contamination of cell cultures). Forming both membranes 22 and 24 from gas permeable membranes allows relative uniform gas exchange and equilibrium in the first liquid medium.

The gas permeable membranes 22 and 24 can also be resistant to cell attachment. This is desirable as it allows cells or tissue 15 (FIG. 2) provided in the bioreactor chamber to be suspended in and remain surrounded by the first liquid medium 31 (e.g., culture or growth medium). Suspending or surrounding the cells or tissue in the first liquid medium, as opposed to allowing them to be attached to one of the membranes 22 and 24, facilitates mass transport of nutrients in the first liquid medium to the cells or tissue. Moreover, suspending the cells or tissue in the first liquid medium reduces competition for nutrients between cells living in a tissue construct and cells attached elsewhere in the bioreactor chamber.

The gas permeable membranes 22 and 24 can be substantially rigid to permit hydrostatic loading of cells or tissue 15 provided in the bioreactor chamber without damage to the cells or tissue 15. The thickness of the gas permeable membranes 22 and 24 will depend on the desired resultant characteristics, which may include, but are not limited to, structural integrity, degree of gas permeability, and rate of transfer of gases.

The gas permeable membranes 22 and 24 can comprise any biocompatible material, which as discussed above is liquid impermeable, capable of allowing transfer of gases into and out of the bioreactor chamber, and capable of excluding microbial contamination. The biocompatible material may be resistant to attachment by cultured cells and/or tissue and/or be treated with a substance that imparts the biocompatible material with a resistance to attachment by cells and/or tissue.

Gas permeable membranes formed from biocompatible materials are known in the art. These membranes typically comprise suitable polymers that may include polystyrene, polyethylene, polycarbonate, polyolefin, ethylene vinyl acetate, polypropylene, polysulfone, polytetrafluoroethylene, or a silicone copolymer. The choice of the composition of the gas permeable membrane will depend on the type of cell to be cultured, degree of gas permeability, rate of transfer of gases, and optical transparency and clarity. For example, the gas permeable membranes 22 and 24 can be a fluoro-ethylene-propylene (FEP) membrane (e.g., FEP (Teflon®) membranes). The gas permeability of FEP is quite good for biologically relevant gases at nominally $1.6 \times 10^3$ and $25.9 \times 10^3$ $cm^3/m^2$-day-atm for $O_2$ and $CO_2$, respectively across a 0.026 mm film at 25° C.

The first membrane 22 and the second membrane 24 can be of a sufficient optical transparency and clarity so as to permit observation during culture, such as of the color of the tissue culture medium, and of cellular characteristics (e.g., growth and morphology of cells such as by microscopy). For example, the first membrane 22 and the second membrane 24 can be of a sufficient optical transparency and clarity so as to observe during culture, changes in the color of the medium's pH indicator. Additionally, both membranes 22 and 24 can be of a sufficient optical transparency and clarity so that when bioreactor chamber 30 is analyzed, for example with a microscope, the cells or tissue therein may be visually analyzed for cell shape, cell number, and additional cell characteristics that typically can be observed by light microscopy.

Optionally, one of the membranes 22 and 24 or at least a portion of at least one of the membranes 22 and 24 can be substantially gas impermeable, that is incapable of exchanging gas sufficiently to support the growth of cultured cells in the absence of another source for gas exchange. For example, it may be desirable for a portion of both membranes 22 and 24 to be gas-impermeable in order for diagnostic applications. In this application, the contents of the bioreactor chamber 30 can isolated so as to measure oxygen consumption.

The gas impermeable membranes or gas impermeable portions of the membrane can comprise a biocompatible material, which is liquid impermeable, is capable of excluding microbial contamination (e.g., pore size is sufficiently small enough to exclude passage of microbes commonly encountered in contamination of cell cultures), and is optically transparent and clear for permitting observation during the cell culture process. Thickness and/or choice of composition of the impermeable membrane will depend on the desired resultant. The impermeable membrane may be comprised of one or more membranes known in the art. The impermeable membrane may be treated, on a side of the membrane to prevent attachment of anchorage-dependent cells in culture.

The membranes 22 and 24 are secured to the first surface 32 and the second surface 34 of the inner frame 20 in a leak-proof sealing manner using a first gasket 90 and a second gasket 92. The first gasket 90 and the second gasket 92 have an annular configuration similar in shape to the inner frame 20 and comprise a material (e.g., silicone rubber) that readily forms a leak-proof seal between inner frame 20 and the first and second membranes 22 and 24.

Optionally, although not shown, a chemical means, such as an adhesive agent (also encompassing a bonding agent) may be used to secure the first membrane 22 and the second membrane 24 to the frame 20 in a leak-proof sealing manner. The adhesive agent may be in the form of a double-faced adhesive tape, a polymeric adhesive, a pressure-sensitive acrylic adhesive, hot-melt adhesive, rubber cement, or any other form of adhesive or bonding agent useful for the purposes attendant to the present invention. Other suitable means may include one or more of heat bonding, sonic welding, pressure fit sealing in forming a leak-proof seal, and a molding process in which the membranes 22 and 24 become an integral part of the frame 20. For example, the adhesive agent can be applied between the frame 20 and portions of the membranes 22 and 24 that extend over the frame 20. Pressure may be applied to cause a force along the portion of the membranes 22 and 24 being secured to the frame in a manner, which results in a leak-proof sealing between the membranes 22 and 24, and the frame 20.

Outer frames 26 and 28 in conjunction with a plurality of screws 94 and nuts 96 are used to secure the membranes 22 and 24 and gaskets 90 and 92 to the inner frame 20. It will be appreciated that other mechanical means (e.g., clamps) or other suitable means can be used to secure the membranes 22 and 24 and the gaskets 90 and 92 to the inner frame 20. The outer frames 26 and 28 can have substantially rectangular shapes that can accommodate the aligning, contacting and securing thereto (in a leak-proof sealing) the membranes 22 and 24 to the inner frame 20 in assembling bioreactor housing 12. The outer frames 26 and 28 can include openings 100 and 102 that can form a first outer chamber 104 and a second outer chamber 106 (FIG. 2) for receiving a second liquid medium 110, which can be readily pressurized. By readily pressurizing the second liquid medium 110 provided in the outer chambers 104 and 106, continuous or cyclic hydrostatic pressure in the MPa range can be provided through the gas permeable membranes 22 and 24 to the bioreactor chamber 30. The outer frames 26 and 28 can be formed from a substantially rigid material, such as a metal (e.g., aluminum, anodized aluminum, and steel). It will be appreciated by one skilled in the art that other materials can be used to form the outer frames 26 and 28.

Figure 7:
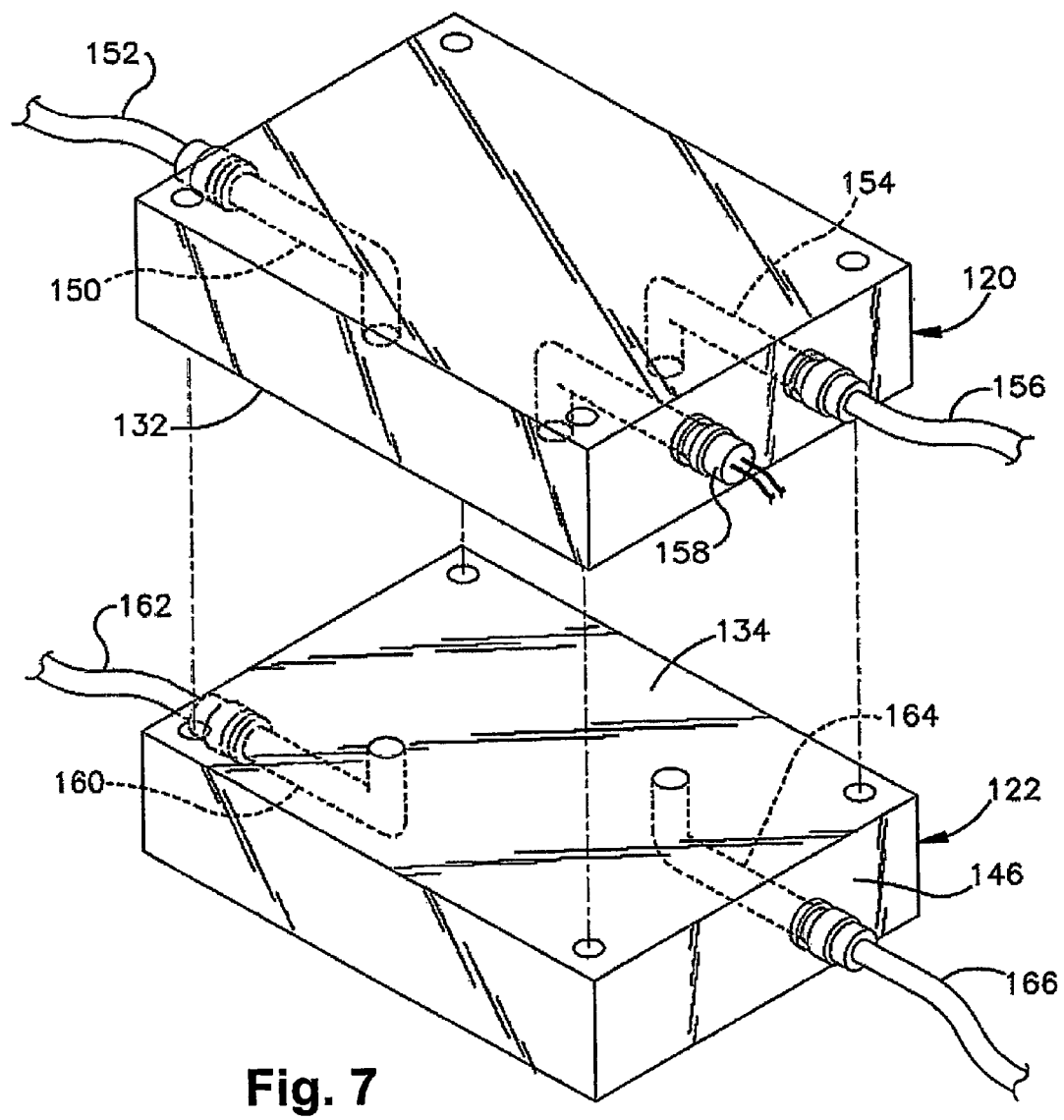
FIG. 7 illustrates a schematic perspective view of a hydrostatic loading module of the bioreactor system in accordance with an aspect of the invention.

FIG. 7 is a schematic perspective view of the hydrostatic loading module 14 in accordance with the present invention. The hydrostatic loading module 14 includes a first member 120 and a second member 122 that provides continuous or cyclic hydrostatic pressure in the MPa range to the contents of the bioreactor chamber 30. The continuous or cyclic hydrostatic pressure is provided using the second liquid medium 110, which can be pressurized to transmit hydrostatic pressure through the gas permeable membranes 22 and 24 to the bioreactor chamber 30. The second liquid medium 110 can include a liquid, such as water, that can equilibrated with a gas, such as air and/or $CO_2$ (e.g., 7.5% $CO_2$ in air) to adjust the environment of the bioreactor chamber. The gas equilibrated into the second liquid medium 110 can be exchanged across the gas permeable membranes 22 and 24 into the first liquid medium 31 contained in the bioreactor chamber 30. The second liquid medium 110 can also be heated or cooled by a heating or cooling means (not shown) to modulate the temperature first liquid medium 31 contained in the bioreactor chamber 30 and control the temperature of the bioreactor chamber 30 during culturing or incubation of the cells or tissue 15.

Referring to FIG. 2, the first member 120 and the second member 122 have substantially rectangular shapes with substantially planar inner surfaces 132 and 134 and substantially planar outer surfaces 136 and 138 that extend between first ends 140 and 142 and second ends 144 and 146. The inner surfaces 132 and 134 of the first member 120 and the second member 122 are coupled respectively to the outer frames 26 and 28 to form the first outer chamber 104 and the second outer chamber 106. The first member 120 and the second member 122 can be formed from a substantially rigid material, such as a substantially rigid plastic. The plastic (e.g., poly(methylmethacrylate)) can be optically transparent so that the contents of the bioreactor chamber 30 can be readily viewed when the first member 120 and second member 122 of the hydrostatic loading module 14 are coupled to the bioreactor housing 12.

The first member 120 includes an inlet channel 150 that is coupled to a feed conduit or line 152 and an outlet channel 154 that is coupled to an exhaust conduit or line 156. The inlet channel 150 extends through the first member 120 from the first end 140 to an area of the inner surface 132 aligned with the first outer chamber 104. The outlet channel 154 extends through the first member 120 from an area of inner surface 132 aligned with the first outer chamber 104 to the second end 144. The inlet channel 150 and the outlet channel 154 allow the second liquid medium 110 to be continuously or cyclically pumped with a computer controlled pump (e.g., gear pump, not shown) to generate pressures in the MPa range in the first outer chamber 104.

Referring to FIG. 7, the first member 120 can also include a pressure sensor 158 (e.g., SenSym-ICT) that monitors the pressure in the first outer chamber 104. The pressure sensor can be connected to a computer (not shown) that modulates the output flow and pressure of pumps (not shown) that supply the second liquid medium 110 to the first outer chamber 104 and the second outer chamber 106.

Referring again to FIG. 2, the second member 122, like the first member 120, includes an inlet channel 160 that is coupled to a feed conduit or line 162 and an outlet channel 164 that is coupled to an exhaust conduit or line 166. The inlet channel 160 extends through the second member 122 from the first end 142 to an area of the inner surface 134 aligned with the second outer chamber 106. The outlet channel 164 extends through second member 122 from an area of inner surface 134 aligned with the second outer chamber 106 to the second end 146. The inlet channel 160 and the outlet channel 164 of the second member 122 allow the second liquid medium 110 to be continuously or cyclically pumped using the computer controlled pumps to generate pressures in the MPa range in the second outer chamber 106.

The first member 120 and the second member 122 can be coupled to the first outer frame 26 and the second outer 28 frame in a leak-proof sealing manner using gaskets 200 and 202. The gaskets 200 and 202 can have an annular configuration similar in shape to the first outer frame 26 and the second outer frame 28 and comprise a material (e.g., silicone rubber) that readily forms a leak-proof seal between the members 120 and 122 and the outer frames 26 and 28.

Outer frames 210 and 212 can be sandwiched about the first member 120, the second member 122, and the gaskets 200 and 202 to secure the first member 120, the second member 122, and gaskets 200 and 202 to the bioreactor housing 12. The outer frames 210 and 212 are coupled to one another with screws 220 and 222. It will be appreciated that the outer frames 210 and 212 can secure the first and second members 120 and 122 and the gaskets 200 and 202 to the bioreactor housing 12 using other mechanical means (e.g., clamps) or other suitable means. The outer frames 210 and 212 can have substantially rectangular shapes that can accommodate the aligning, contacting and securing thereto (in a leak-proof sealing) first member 120 and the second member 122 to the first outer frame 26 and second outer frame 28. The outer frames 210 and 212 can include openings 230 and 232 that allow the content of the bioreactor chamber 30 to be viewed when the bioreactor system 10 is assembled. The outer frames 210 and 213 can be formed from a substantially rigid material, such as a metal (e.g., aluminum). It will be appreciated by one skilled in the art that other materials can be used to form the outer frames 210 and 212.

During operation of the bioreactor system 10, the first liquid medium 31 can be readily perfused through the bioreactor chamber 30 using a pump (not shown) and the second liquid medium 110 can be readily perfused through first outer chamber 104 and the second outer chamber 106. When pressurizing the bioreactor chamber 30, the inlet port 50 and the outlet port 52 are closed using medium control valves 60 and 62. The hydrostatic pressure in the first and the second outer chambers 104 and 106 is increased and hydrostatic pressure is applied across the gas permeable membranes 22 and 24 to the bioreactor chamber 30. Pressure in the chamber 30 is monitored by the pressure sensor 158 and modulated by controlling pump speed and a flow outlet restrictor (not shown) with a computer. This design allows the application of arbitrary hydrostatic pressure waveforms and physiologically relevant hydrostatic loading of cells or tissue 15 cultured, grown, or incubated in the bioreactor chamber 30 without removing the specimen or otherwise breaching the bioreactor system 10. Additionally by physically separating the pressurization and perfusion circuits, pressurization of the culture or growth medium is avoided. This mitigates denaturing proteins potentially provided in the culture or growth medium and removes the pumps as a source of contamination for the culture or growth medium. Further, the addition of the hydrostatic loading module does not alter the geometry of the basic bioreactor chamber, thus allowing for well-controlled experiments and computer modeling.

Figure 8:
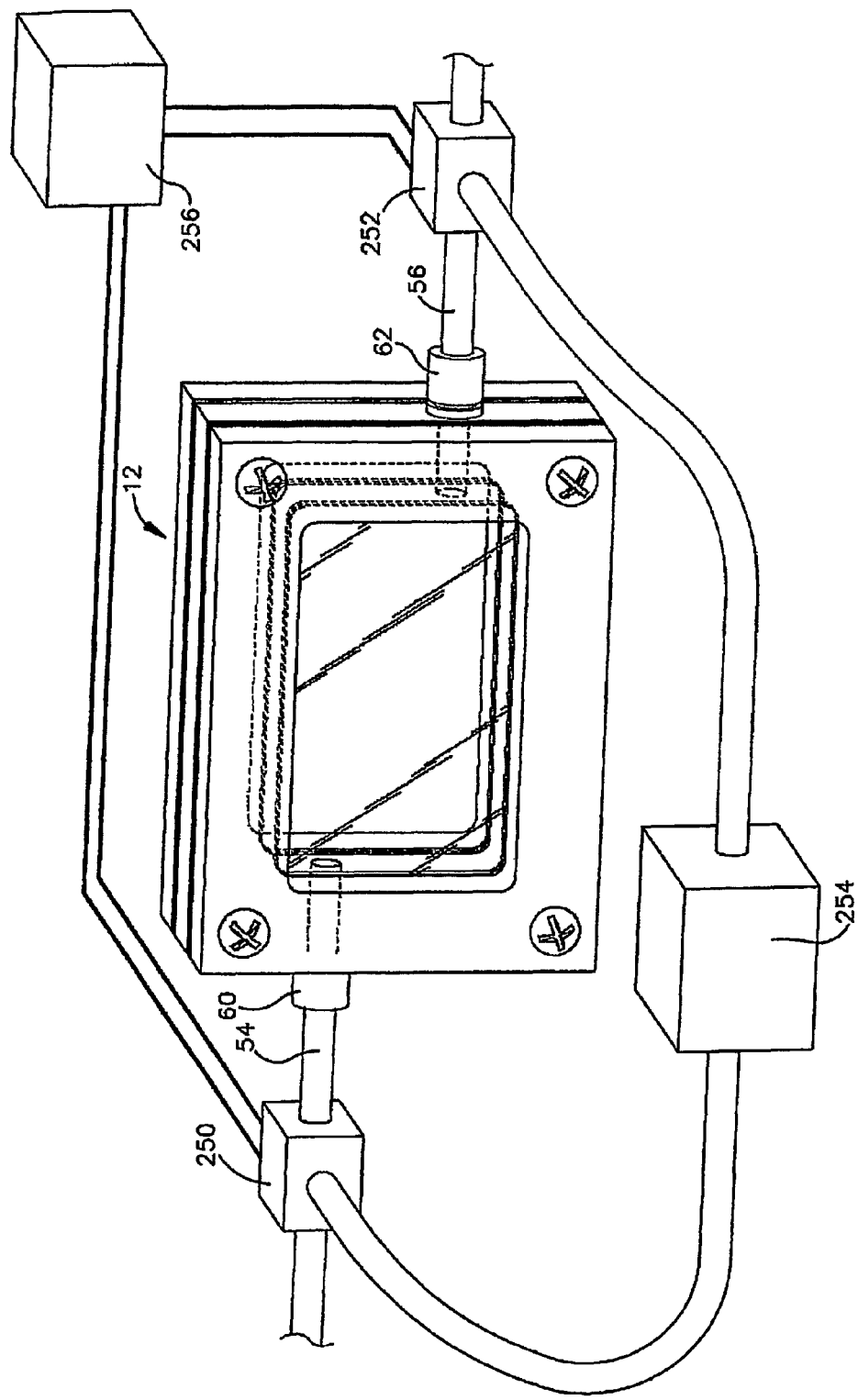
FIG. 8 illustrates a schematic perspective view of a spectrophotometer in accordance with another aspect of the invention.

The bioreactor system 10 in accordance with the invention can further include monitoring systems and modules that can be used to monitor and control the culture media, the bioreactor chamber environment, and the growth of the cells or tissue in the bioreactor chamber. By way of example, as shown in FIG. 8, flow-through spectrophotometric cuvettes 250 and 252 can be fitted on the feed line 54 and exhaust line 56 of the bioreactor housing 12. The flow-through cuvettes 250 and 252 can be connected by optical fibers to a multi-channel fiber-optic spectrophotometer 254. Electrical sensor leads can also connect the cuvettes to a computer 256. The spectrophotometer 254 can measure light transmission and absorbance of at least one molecular species in the culture medium that flows through the feed line 54 and exhaust line 56. For example, the spectrophotometer can capture absorption spectra at 559 nm of phenol red added to the culture medium. The spectrophotometer 254 can include a monochromator (not shown) that can be modified to position polished ends of optical fibers (e.g., 500 μm) in an output slit plane. The wavelength can be adjusted using a stepper motor (e.g., 40 steps/nm). The cuvette holders can align the collimated output from each fiber, the cuvette, and a detector-amplifier hybrid. Data collection and control can be synchronized using custom software. The correlation ($r^2$=0.998) between pH and transmission at 559 nm in the physiologically relevant range permits calibration of the device in pH units.

Other environmental parameters can also be monitored and controlled. These other environmental parameters can include temperature, solute concentration, and oxygenation, $CO_2$ concentration, and glucose concentration. It will be appreciated by one skilled in the art that still other selected products or conditions can also be monitored or affected. In one aspect of the invention the monitoring system can be set to clamp selected environmental parameters at predetermined values, while allowing others to float as outcome variables, and can be set to flag specific conditions as requiring intervention.

The bioreactor system 10 in accordance with the present invention can be used to culture cells, whether the cells are individual cells (cells which are grown independent of forming a structure such as a tissue; an illustrative example being a cell line), or cells forming a tissue (typically, a mesh or network of cells, with their intercellular substance in forming a structured or organized tissue), or a combination thereof. It will be apparent to one skilled in the art that individual cells which can be cultured in the bioreactor system comprise one or more cell types including, but not limited to, animal cells, insect cells, mammalian cells, human cells, transgenic cells, genetically engineered cells, transformed cells, cell lines, anchorage-dependent cells, and anchorage-independent cells. It will be also apparent to one skilled in the art, that tissue formed by cells in culture can also be cultured in the bioreactor system according to the present invention. It will further be apparent to one skilled in the art that the bioreactor system of the present invention is generally not limited to a specific type of cell to be cultured, nor the tissue culture medium capable of sustaining cell growth as long as the medium provides sufficient nutrients and properties (e.g., osmotic pressure) to maintain and support cell growth.

Figure 9:
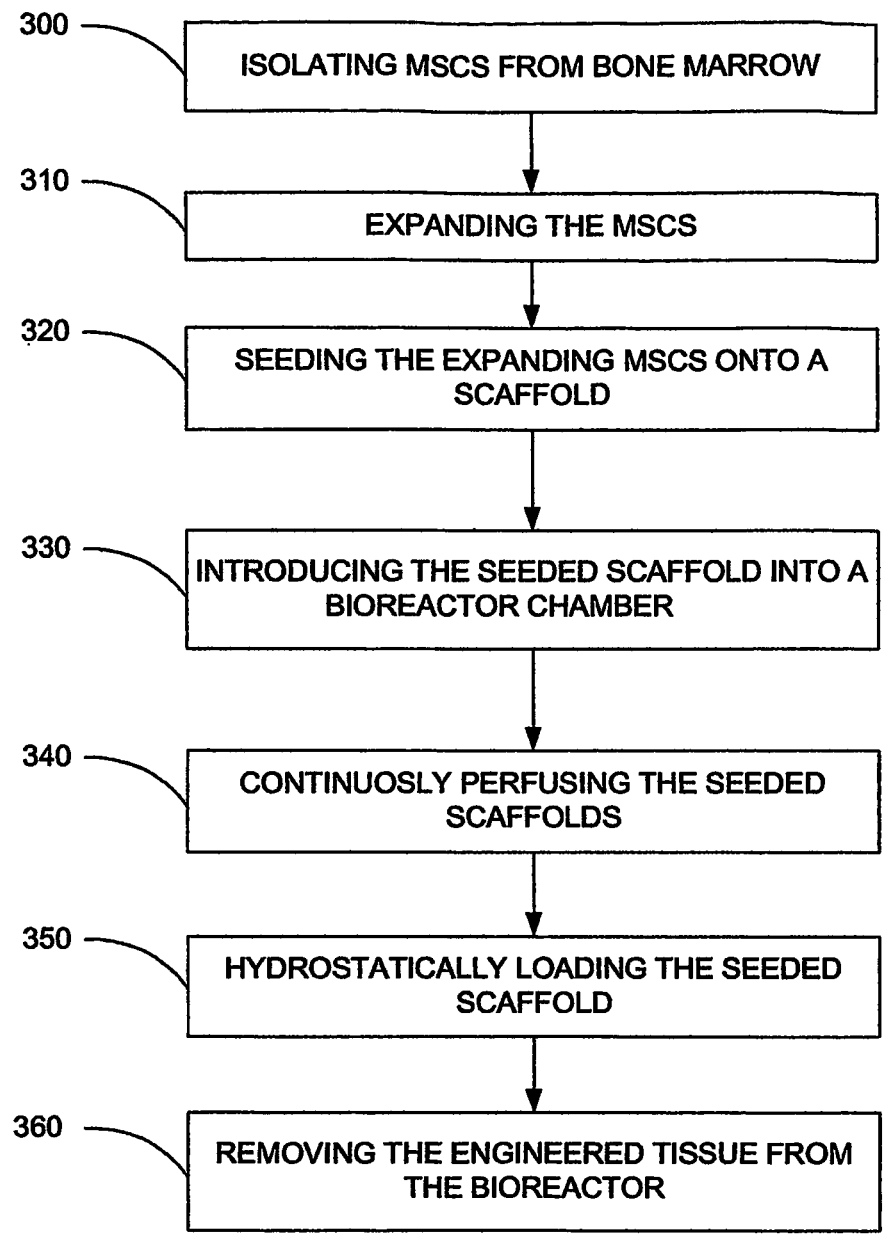
FIG. 9 illustrates a flow diagram of a tissue engineering method in accordance with an aspect of the invention.

In accordance with an aspect of the invention, bone marrow derived mesenchymal stem cells (MSCs) can be cultured or grown in the bioreactor system to form chondrogenic tissue for articular cartilage repair. FIG. 9 is a flow diagram illustrating a method of culturing or growing bone marrow derived MSCs in the bioreactor system of the present invention to form chondrogenic tissue for articular cartilage repair.

In the method, at 300, MSCs are isolated from bone marrow using known techniques, such as those described in U.S. Pat. Nos. 5,591,625, 5,643,736, 5,736,396, and 6,087,113 as well as Haynesworth et al., *Characterization of cells with osteogenic potential from human bone marrow*. Bone, 1992. 13:81-88; Bruder et al. *Growth kinetics, self-renewal, and the osteogenic potential of purified human mesenchymal stein cells during extensive subcultivation and following cryo-preservation*. Journal of Cellular Biochemistry, 1997. 64(2): 278-294; and Lennon et al., *Human and animal mesenchymal progenitor cells from bone marrow: Identification of serum for optimal selection and proliferation*. In Vitro Cellular and Developmental Biology, 1996. 32(10):602-611, all of which are herein incorporated by reference in their entirety. The bone marrow can derived from the patient being treated, such that the MSCs are autologous, or from other individuals, such that the MSCs are allogeneic. The number MSCs isolated form the bone marrow can vary and can include, for example, about 200,000 to about 250,000 MSCs.

At 310, the isolated MSCs are expanded in culture. The expansion of the MSCs can be performed without loss of their multipotentiality using cell-culturing procedures. For example, the MSCs can be can be culture-expanded in two passages in a culture medium of DMEM and 10% fetal bovine serum (FBS) provided in culture vessel. The FBS in the culture medium provides selective attachment of the MSCs, mitotic expansion, and maintenance of the MSC phenotype. A typical culture-expanded preparation yields about $400 \times 10^6$ to about $600 \times 10^6$ cells.

At 320, the expanded MSCs are seeded onto a porous (i.e., open celled) constructs (e.g., scaffolds or sponges) by, for example, vacuum seeding. In one vacuum seeding method, the cells are suspended in a volume of medium equal to the retention volume of the scaffold and drawn into the scaffold by the repeated brief applications of a vacuum (−27"Hg) (e.g., a 14×5 mm HYAFF®-11 sponge will hold 750 μl of medium). The technique is rapid (e.g., minutes), and yields near-quantitative seeding of the cells with a very uniform distribution throughout the scaffold even at very high cell densities The MSCs can be seeded at a density, for example, of about $10^8$ cells/ml. The scaffold may or may not be biodegradable depending on the intended application. Examples of scaffolds can include hyaluronan-based scaffolds (Hyaff-11, Fidia, IT), gelfoam, sponges, such as collagen-based sponges (e.g., collagen type I, II, and chondroitin sulfate), and PLLA or PLGA-based scaffolds. It will be appreciated by one skilled in the art that other scaffolds can also be used. The scaffolds or sponges can be cut to size and are manageable for loading cells and implanting in vivo. Pore size of the scaffold or sponge can range from about 10 microns to about 400 microns, with a porosity of about 80% or greater.

At 330, the seeded scaffolds (i.e., tissue-engineered constructs) can be introduced into the bioreactor chamber of a bioreactor system in accordance with the present invention. The bioreactor system includes a bioreactor chamber, which can contain a chondrogenic medium, and a hydrostatic loading module for applying hydrostatic pressure to the contents of the bioreactor chamber. The introduction of the cells into the bioreactor chamber can be performed in a sterile environment, or non-sterile environment provided that aseptic technique is used. This is because the bioreactor system itself (when sterilized using conventional means known in the art) can provide a sterile, hermetic environment.

At 340, bioreactor chamber and the MSCs of the tissue-engineered construct introduced into the bioreactor chamber are perfused with a chondrogenic medium. The chondrogenic medium can include any culture medium that promotes chondrogenic differentiation of the MSCs. One example of a chondrogenic medium includes DMEM-HG (4.5 g/l glucose) supplemented with 1% ITS+Premix (625 µg/ml insulin, 625 µg/ml transferrin, 625 ng/ml selenious acid, 125 mg/ml serum albumin and 535 µg/ml linoleic acid; Collaborative Research), 100 µM ascorbate-2P (Wako) $10^{-7}$ M dexamethasone (Sigma) and 10 ng/ml TGF-β1 (R&D Systems). The bioreactor chamber can be perfused at a very low rate (e.g., about 250 µl/hour). This results in essentially neglible shear on the tissue-engineered construct.

At 350, the tissue-engineered construct in the bioreactor chamber is isotropically loaded by applying cyclical hydrostatic pressure from the hydrostatic loading module to the tissue-engineered construct. By way of example, the loading regimen can be 1 hour on, 1 hour off, 24 hours a day, 7 days a week for 21 days. During the "on" hour, hydrostatic load can be applied following a pre-programmed sinusoidal waveform between 0 and 1000 kPa. Hydrostatic loading of the tissue-engineered construct increases the extracellular matrix production and enhances chondrogenesis of the MSCs in the tissue-engineered construct. Mechanical tests of the samples from the hydrostatic loading experiments revealed a 4-fold increase in Young's equilibrium modulus in the loaded compared to matched unloaded control samples. This allows the tissue-engineered construct to more readily develop properties required for survival after implantation in a joint.

After about three weeks in the bioreactor system, the tissue-engineered construct becomes similar to cartilage and the MSCs take on the chondrocyte phenotype. At 360, the tissue-engineered construct is removed from the bioreactor and utilized for its intended purpose.

Figure 10:
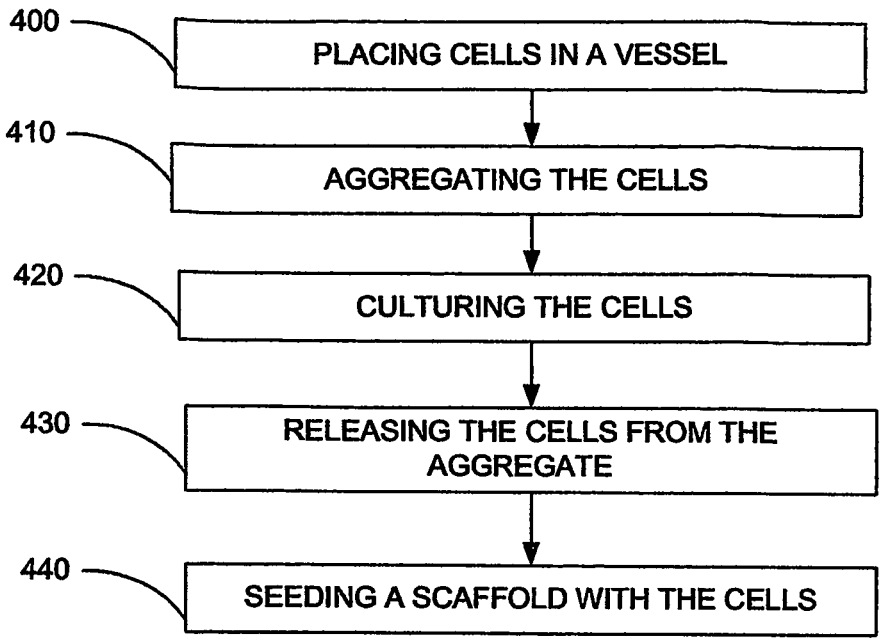
FIG. 10 illustrates a flow diagram of a tissue engineering method in accordance with another aspect of the invention.

Optionally, the MSCs can be manipulated before and after assembly into the scaffolds to reduce the consumption of externally supplied substrates, and thus enhance viability and chondrogenesis. FIG. 10 illustrates one method of manipulating the MSCs to enhance chondrogenesis. In the method, at 400, a suspension of MSCs (e.g., about 200,000 to about 250,000 cells) are placed in a sterile conical-bottomed vessel (e.g., polypropylene vessel). The vessel can contain a culture medium with chondrogenic supplements. At 410, the MSCs contained in the vessel are then centrifuged to aggregate the cells. At 420, the resulting aggregate is maintained in culture for several days to allow chondrogenesis to begin. At 430, after remaining in culture for several days, the MSCs are released from the pellet environment by enzymatic digestion. At 440, the MSCs are then used to seed large-scale tissue-engineered implants, which can then be cultured in the bioreactor system in accordance with the foregoing method of the invention. Use of this method provides markedly enhanced viability throughout the construct, chondrogenic differentiation of cells from MSC preps that otherwise exhibited poor chondrogenic potential, and abundant chondroid extracellular matrix production.

Figure 11:
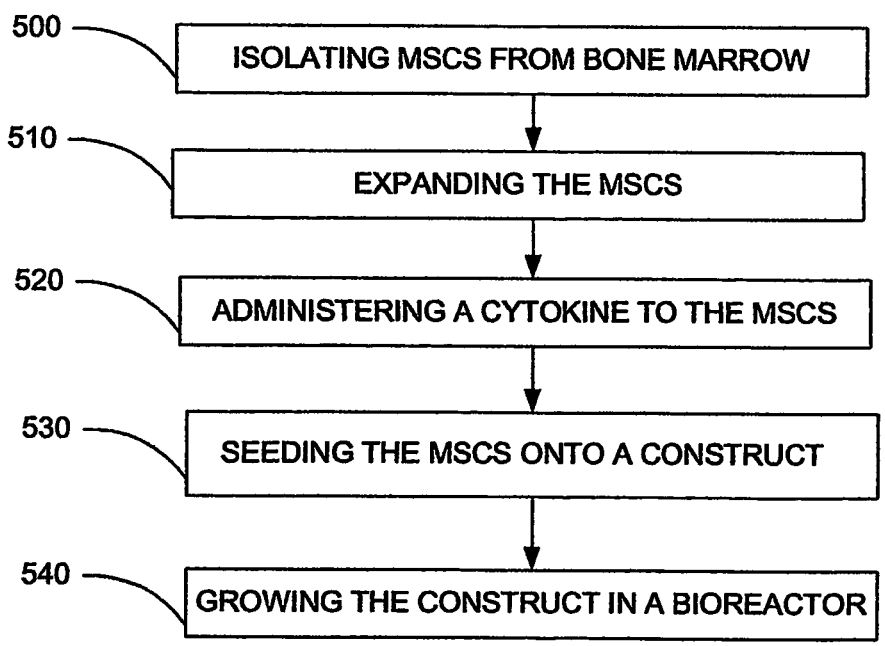
FIG. 11 illustrates a flow diagram of a tissue engineering method in accordance with yet another aspect of the invention.

In another aspect of the invention shown in FIG. 11, a pretreatment regimen can be used to improve chondrogenesis by adult-bone marrow derived MSC. In the method, at 500, bone marrow derived MSCs are isolated from bone marrow biopsies. At 510, the MSCs are then expanded in culture using a standardized set of culture conditions. At 520, a cytokine, such as, recombinant rhFGF-2, is added to the human bone marrow derived MSC at the first medium change (e.g., on days 3 or 4) following isolation from the bone marrow biopsy, and throughout the entire monolayer culture expansion phase. The rhFGF-2 can be added to culture medium, for example, at about 1 to about 10 ng/ml final concentration, and the culture medium can be changed, for example, about two times per week. At 530, the cells can be passaged just prior to confluence and then seeded onto tissue scaffolds (biocompatible constructs). At 540, the assembled constructs can be grown in a continuous perfusion bioreactor with a chondrogenic medium.

Use of this method provides marked enhancement (e.g., about 2 to about 3 fold) of the proliferation rate of the cells in monolayer culture, markedly enhanced expression of markers of chondrogenesis by rhFGF-2 pretreated MSCs exposed to appropriate stimuli, and rescue of MSCs preparations that otherwise displayed poor chondrogenic potential.

Figure 12:
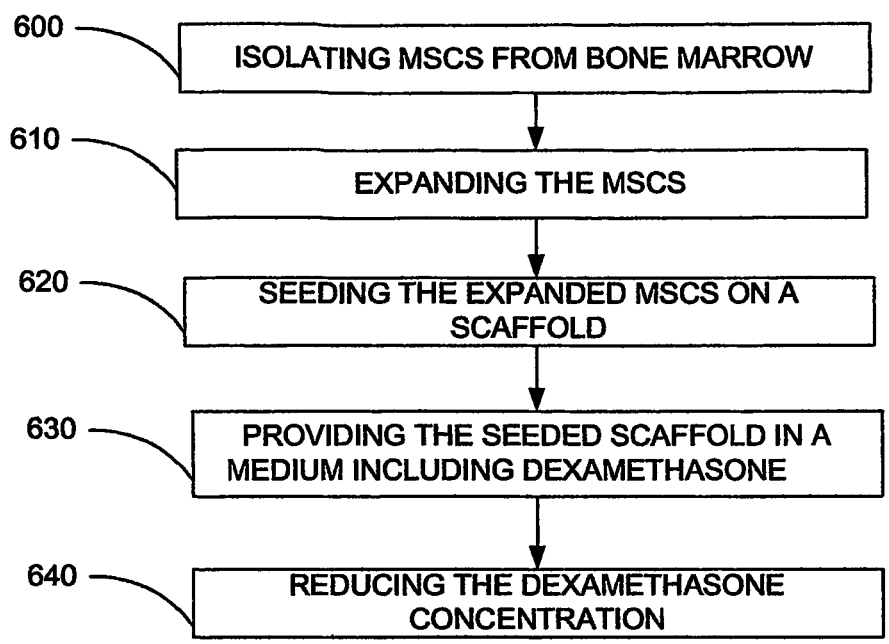
FIG. 12 illustrates a flow diagram of a tissue engineering method in accordance with still another aspect of the invention.

In another method illustrated in FIG. 12, at 600, bone marrow derived MSCs can be isolated from bone marrow biopsies. At 610, the MSCs can then be expanded in culture using a standardized set of culture conditions. At 620, the expanded cells can then be seeded onto constructs (e.g., biocompatible scaffolds). At 630, the assembled constructs can be grown in a continuous perfusion bioreactor with a chondrogenic medium that included dexamethasone (e.g., $10^{-7}$ M). At 640, the dexamethasone concentration can be reduced in order to induce the internal synthesis of BMP-2, a chondrogenic growth factor. Reduction of the dexamethasone promotes improved thickening of the extra-cellular matrix of the construct.

It will be appreciated that although the foregoing was described using MSCs to form cartilage tissue, other cell types can also be used. For example, it will be appreciated that other stem cells as well as other differentiated cells (chondrocytes) can also be used in the method. Moreover, it will be appreciated that the various methods can be used with each other to optimize the formation of the tissue constructs.

EXAMPLES

The following examples serve to illustrate certain preferred embodiments and aspects of the present invention and are not to be construed as limiting the scope thereof.

Example 1

A Multichannel Fiberoptic Spectrophotometer for Monitoring Bioreactor Medium pH

Introduction:

Miniaturized bioreactor systems are becoming an increasingly useful tool in tissue engineering applications. Our laboratory is currently exploring their use for the generation of large cartilage implants for the repair of cartilage defects. In these studies, we assemble mesenchymal precursor cells at very high densities (up to $100 \times 10^6$ cells/ml) and carrier matrices to form composite grafts of up to 2×2 cm. The precursor cells are then induced to differentiate along the chondrogenic pathway in a bioreactor system.

A major technical problem associated with the in vitro maintenance of large constructs, in which tens of millions of cells are bathed in a few ml of culture medium, is the maintenance of an appropriate supply of fresh medium. The replacement rate must be adequate to satisfy the metabolic needs of the cells, to supply needed growth factors, and to wash out waste products). Offsetting this requirement is the goal of not washing out potentially useful autocrine or paracrine factors secreted by the cells.

A useful marker for the extent to which the cell culture medium has been depleted by the cells is the pH of the medium. In our system, replacement rates of 460 μl/hr/(cm$^3$ implant) are sufficient for survival of an implant saturated with MSCs. The medium pH drops from ~7.3-7.4 at the inlet to 6.5 at the outlet of the bioreactor. This drop is dependent on the number and type of cells, their differentiation state, and on the medium replacement rate: the longer the dwell time in the bioreactor, the more acidified the effluent medium. This suggests the possibility to use pH change in a feedback loop to control medium replacement rates. In addition to reflecting medium depletion, low pH has a direct negative impact on cartilage matrix synthesis and degradation. Low extracellular matrix pH modulates the activity of receptors and ion channels on the chondrocyte membrane, and influences the rate of matrix mineralization and the activity of degradative enzymes. Alterations in pH, can shift the balance between matrix synthesis and degradation, alter the mechanical properties of cartilage, and contribute to the destruction of articular cartilage in arthritis.

The purpose of this study was to develop a non-contact optical system to continuously measure the pH of the cell culture medium at the inlet and outlet of multiple bioreactor chambers. Most common cell culture media contain a pH indicator dye, which shifts color from red to yellow in the range of ph usually encountered in cell culture environments. This color shift is due to a strong, pH sensitive light absorption peak at 559 nm of the indicator dye phenol red, and this is exploited in the current approach.

Materials & Methods:

The following components were developed for this project.

Multi-Channel Fiber Optic Spectrophotometer:

As a tunable source of monochromatic light, we used the monochromator from a Beckman model DU-8 spectrophotometer, illuminated by a 12V 50 W tungsten lamp. The monochromator was modified to position the polished ends of 500 μm optical fibers in a 5×13 array in the output slit plane. The monochromator output wavelength can be adjusted dynamically using a computer-controlled stepper motor (0.025 nm/step).

Flow-through cuvettes with a 1 cm optical path length were designed to be positioned at the inlet and outlet of each bioreactor chamber. They can be cleaned and sterilized independently of the cuvette holders.

Cuvette Holder:

The cuvettes are placed in an opaque black Delrin cuvette holder. A modified SMA connector houses and aligns a single fiber, a 1.5 mm sapphire ball lens is used to collimate the light output. A blue-enhanced detector-amplifier hybrid (PDB-716-100, Photonic Detectors Inc.) collects light transmitted through the sample. The output voltage is read on a HP 3421A voltmeter. Data collection and stepper motor control are synchronized using custom PC based software.

Test Samples:

To ensure accurate test pH values, samples were 200 mM phosphate buffer adjusted to pH 6.75 to 7.50 in 0.05 pH increments. All contained phenol red at 15 mg/l—identical to most commercial medium formulations. pH of the test samples was verified using an Accumet pH meter with a glass Ag/AgCl electrode. In the wavelength range (400-700 nm) tested, these samples had absorption spectra which were essentially indistinguishable from that of normal culture medium. Test samples were drawn into the cuvette and then scanned from about 400 nm to about 700 nm. Cuvettes were flushed with dH$_2$O between readings.

Figure 13:
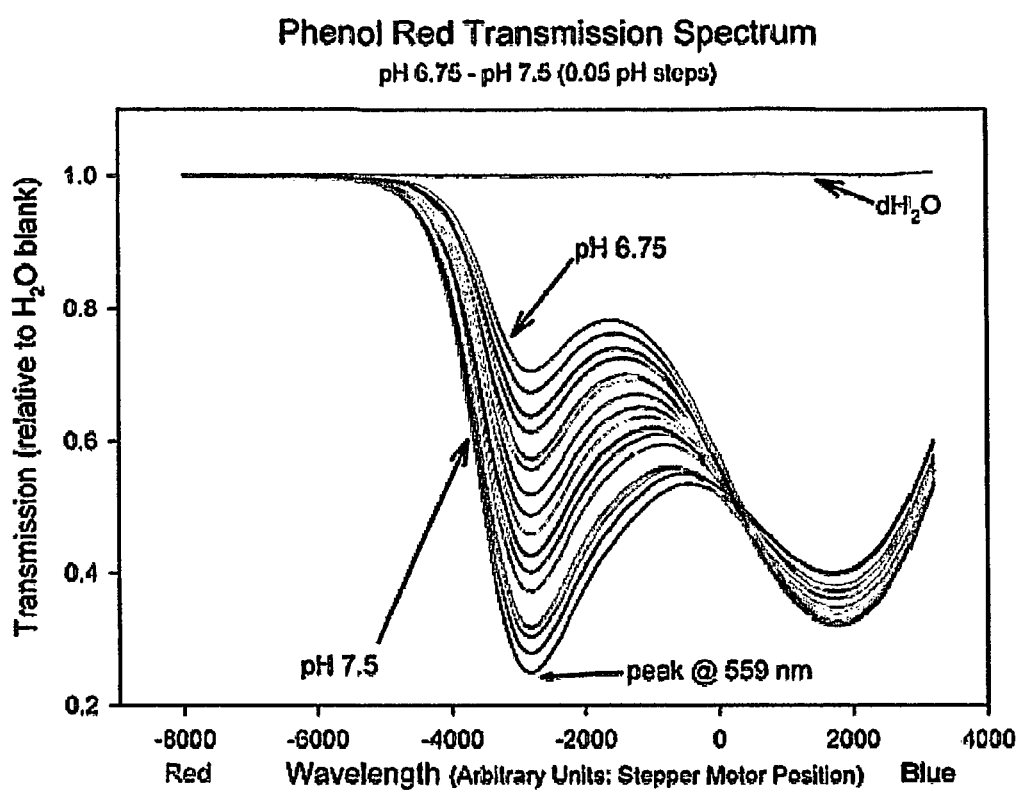
FIG. 13 is a plot illustrating phenol red transmission spectra at pH 6.75 to 7.5 from a spectrophotometer in accordance with an aspect of the invention.

Results Summary:

FIG. 13 is a plot illustrating phenol red absorption spectra were successfully captured using the multi-channel fiber optic spectrophotometer. The predicted peak absorption at 559 nm was readily detectable. A scan of deionized water was used as a blank to normalize all the spectra, to account for spectral non-linearities in the optical components of the system. pH differences of 0.05 units were readily resolved using only the transmission at 559 nm. Better resolution can be expected with sampling at more wavelengths.

Figure 14:
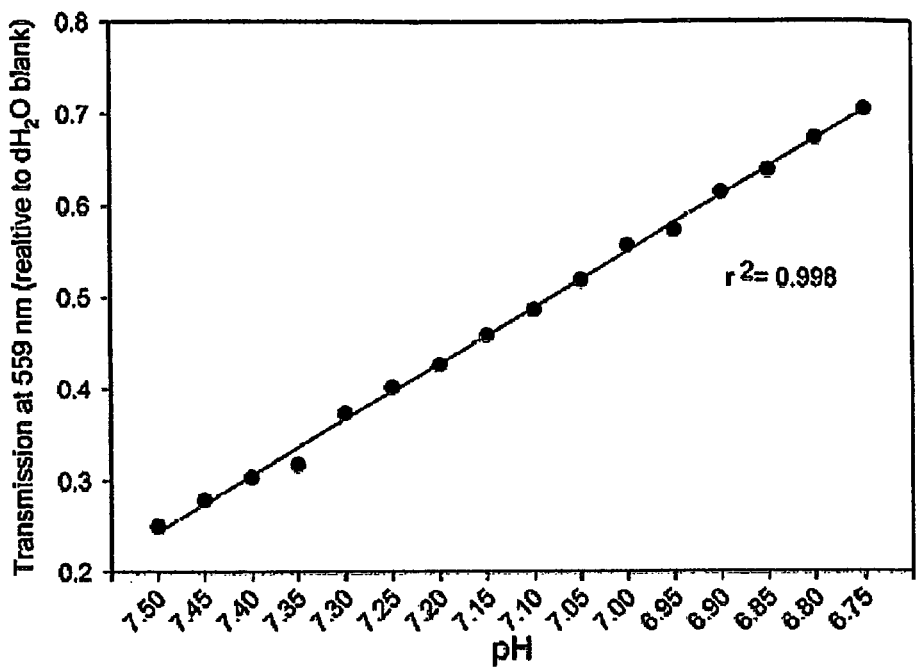
FIG. 14 is a plot illustrating the correlation between test buffers and transmission at 559 nm.

FIG. 14 is a plot illustrating the strong, linear, correlation ($r^2$=0.998) between pH and transmission at 559 nm in the physiologically relevant range permits easy calibration of the device in pH units. Repeat measurements of the same samples correlated with an $r^2$ of better than 0.99999.

Figure 15:
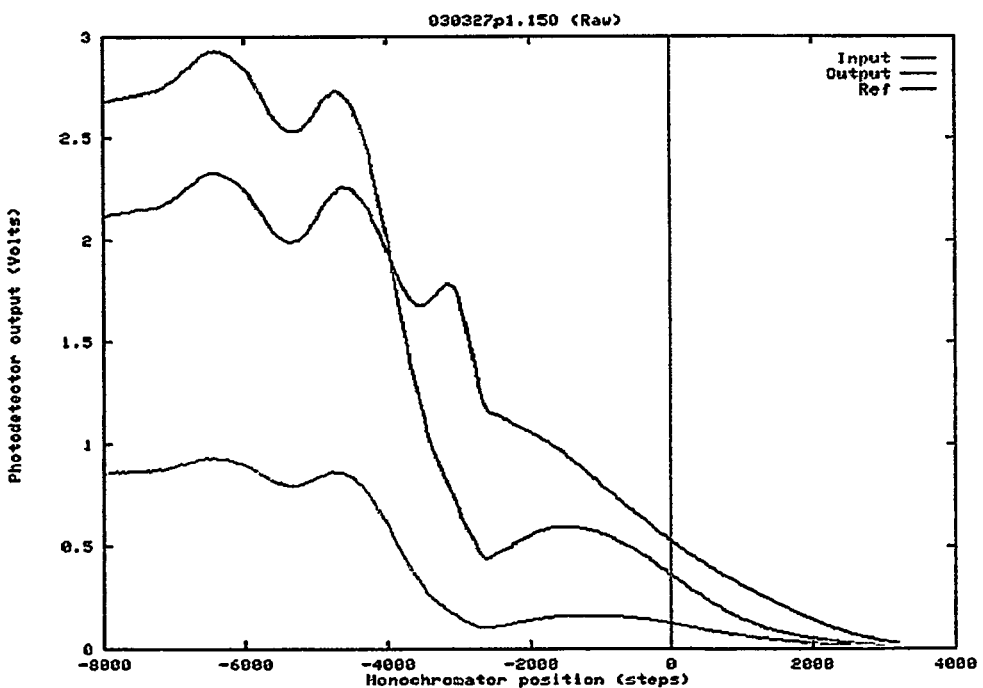
FIG. 15 is a plot illustrating raw data taken from a spectrophotometer in accordance with an aspect of the invention.
Figure 16:
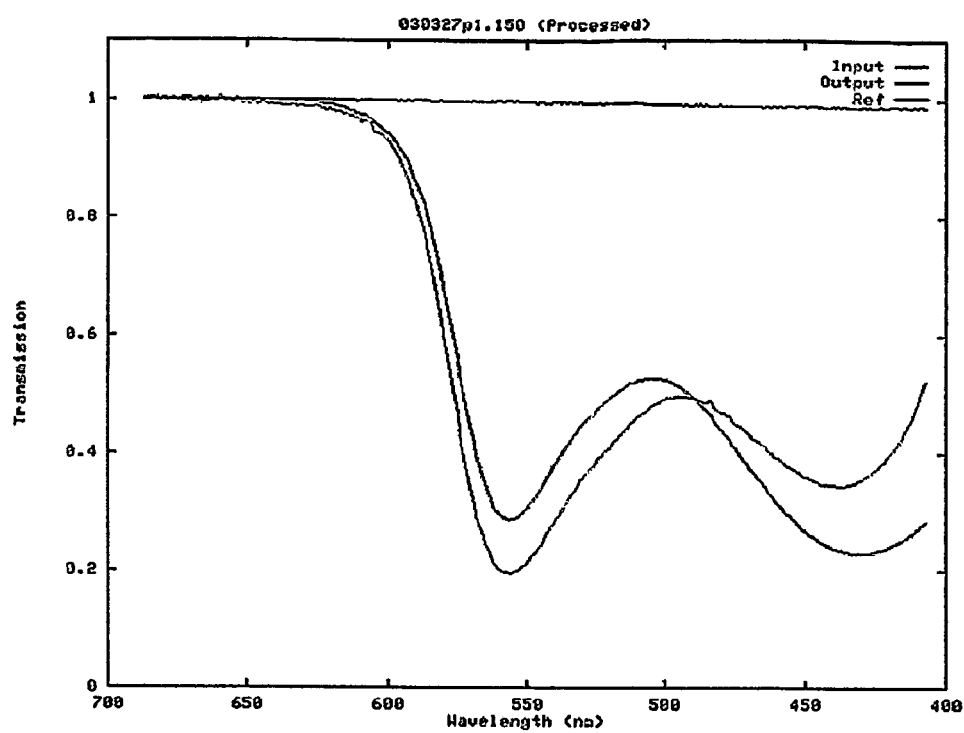
FIG. 16 is a plot illustrating the raw data of FIG. 13 after it has been processed.

Three channels of data are currently collected. FIGS. 15 and 16 illustrate, respectively, raw and processed data taken from the instrument. In addition to the inlet and outlet of the bioreactor, a water-filled cuvette serves as a blank to normalize the readings. Although only 3 channels are currently used, the system allows expansion up to 65.

Our immediate goal in designing this system was to use the medium pH as a marker for the extent to which the culture medium in the bioreactor had been metabolized. Our fiber optic spectrophotometer appears suitable for this task. Major advantages of this device include that the medium pH can be continuously sampled in a non-contact manner, without breaching an otherwise closed bioreactor system, and that a large number of channels can be sampled simultaneously.

Output from this device can be used to measure the rate at which cells deplete their culture medium at a given flow rate. In addition, this information can be used to continuously modulate the media flow rates in the bioreactor using medium pH as the control variable, to maintain the pH within a desired range. Alternatively, the output could be used to modulate the pH by controlling the PCO$_2$ in the incubator.

We have also developed a prototype for a 65-channel fiber-optic spectrophotometer, which can perform accurate real-time non-contact measurement of the medium pH at the inlet and outlet of multiple bioreactors). Flow-through cuvettes with a 1 cm optical path length are positioned at the inlet and outlet of each chamber. They can be cleaned and sterilized independently of the cuvette holders. A water-filled cuvette is used as a blank. The cuvettes are placed in an opaque black Delrin® cuvette holder. Light output from a stepper motor-controlled monochromator is fed to the cuvette via 500 μm fibers. A modified SMA connector houses and aligns each optical fiber; a 2 mm BK-7 ball lens is used to collimate the light output. A blue-enhanced detector-amplifier hybrid (PDB-716-100, Photonic Detectors Inc.) collects light transmitted through the sample. The output voltage is read on a HP 3478A voltmeter. Data collection and stepper motor control are synchronized using custom PC-based software. The measurements can be made in the incubator, without breaching the sterility of the bioreactor or changing the environmental conditions. A PC running custom FORTRAN software controls the monochromator position and records the photodetector outputs to disk. At the end of each scan, the data files are processed by a script, graphed, and the results are posted to a web page. A resolution of 0.05 pH units can be achieved using only the absorption peak at 559 nm, which is sufficient for our purposes. By processing more of the spectrum, we could improve the resolution considerably.

Example 2

A Pre-Treatment Regimen to Improve Chondrogenesis by Adult Bone-Marrow Derived Mesenchymal Progenitor Cells Background:

Successful tissue engineering of articular cartilage has the potential to revolutionize the therapy of degenerative joint disease. Adult human mesenchymal stem cells (hMSCs) are attractive candidates for this role due to their documented osteogenic and chondrogenic potential, and ease of harvest and mitotic expansion. For this purpose, mesenchymal stem cells have to be harvested from the donor, and expanded in culture, sometimes considerably, in order to obtain sufficient numbers of cells to seed biodegradable scaffolds at high densities. To obviate immunological complications, the use of autologous cells is preferred. The cells are isolated from a bone marrow biopsy and must be expanded in culture. This adds a lag time of several weeks between the initial harvest of the cells, and the implantation of the completed construct into the cartilage lesion. Any approach which has the potential to shorten this interval, or to improve the creation of the construct, would therefore be desirable.

Growth factors have the capacity to modulate or modify the phenotype of cells exposed to them. Desirable modulations of the phenotype which can improve the tissue engineering process include: enhancement of mitogenic potential (which results in a significantly shortened time in culture), maintenance of a pluripotential, or enhancement of the chondrogenic potential In preliminary tests of this method, as outlined below, we have achieved at least two of these three desired modulations.

Methods:

Bone marrow derived mesenchymal stem cells were isolated from marrow biopsies following standard published procedures. The cells were then expanded in culture using a standardized set of culture conditions. The cell preparations were subjected to a density gradient and plated in control medium (DMEM-LG+10% FBS). Our modification to the method consists in the addition of recombinant human FGF-2 (rhFGF-2) to the human bone-marrow derived mesenchymal stem cell culture at the first medium change on days 3 or 4 following isolation from the bone marrow biopsy, and throughout the entire monolayer culture expansion phase. The rhFGF-2 was added to the culture medium at 1-10 ng/ml final concentration, and the culture medium is changed 2 times per week. Cells are passaged just prior to confluence.

At the first medium change, (day 4) the human bone-marrow derived mesenchymal cellcultures either received control medium, or medium supplemented with rhFGF-2 at 10 ng/ml. Cell numbers and size were evaluated by flow cytometry at the end of primary and first passage; at the end of first passage each subpopulation was introduced into aggregate culture to induce chondrogenic differentiation. No rhFGF-2 was present in the aggregate culture medium. RNA was extracted at the end of first passage, and gene expression profiles for each group were generated using the Affymetrix HG-U133A chip. Pairwise comparisons using the Affymetrix MAS algorithm and conservative acceptance criteria were used to identify differential gene expression.

Figure 17A:
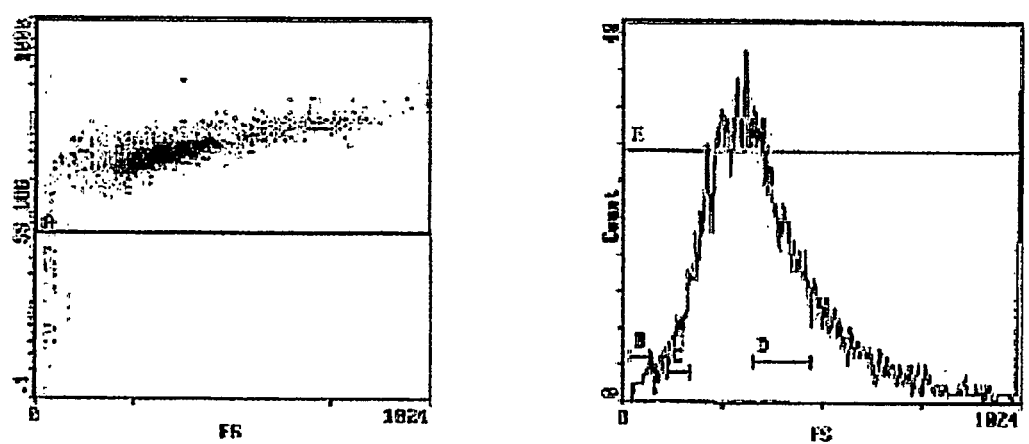
FIGS. 17A, 17B, and 17C are plots illustrating forward scatter analysis of control hMSCs (top) and rhFGF-2 treated hMSCs (bottom).
Figure 17B:
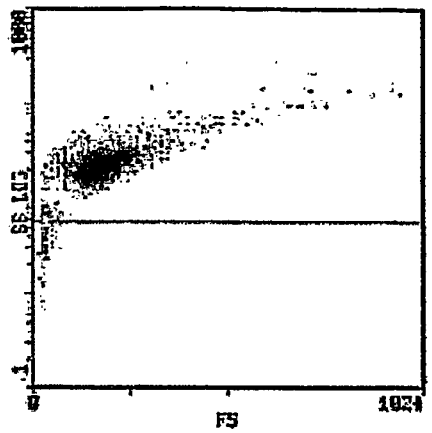
Figure 17B:
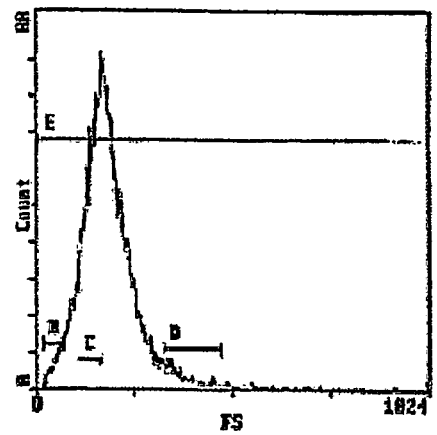
Figure 17C:
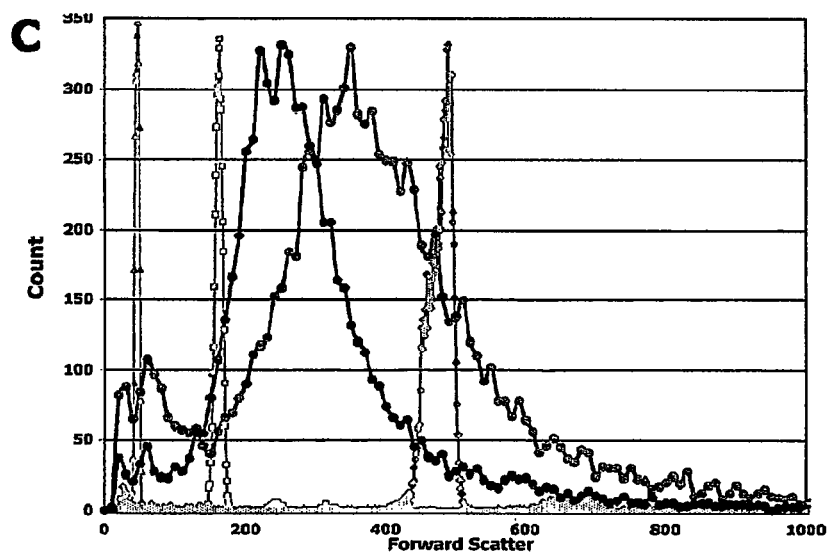

Results:

Mitotic Effects:

Human MSCs expanded in the presence of rhFGF-2 exhibit shorter population doubling times and are reproducibly smaller than those maintained in control conditions (FIGS. 17A and 17B).

Figure 18:
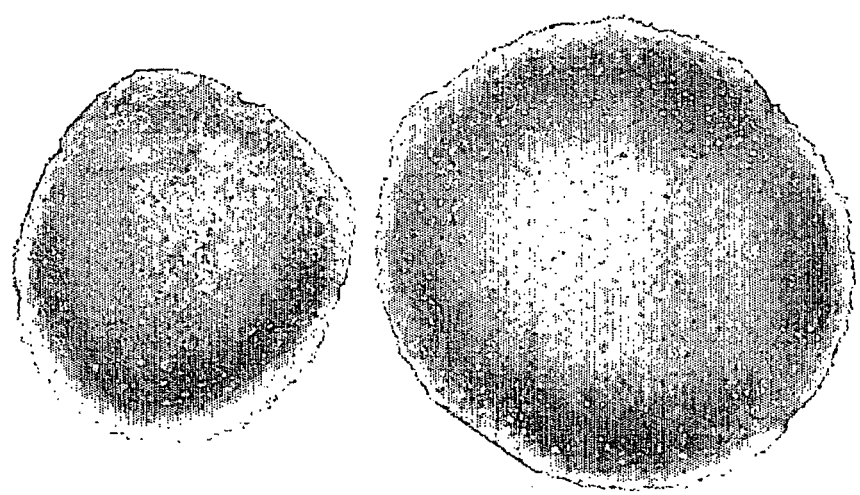
FIG. 18 is a microphotograph illustrating aggregates made with control (left) and rhFGF-2 treated after 3-weeks in chondrogenic medium.

Chondrogenic Potential:

rhFGF-2 treated cells produce aggregates that differentiate more rapidly and are significantly larger and more homogeneous (FIG. 18) than those generated with control cells.

Microarray analysis yielded a database of more than 700 genes differentially expressed (2-fold or greater change) in the two groups.

Discussion & Conclusions:

Exposure of hMSCs to rhFGF-2 during mitotic expansion increases cell yield and shortens time in culture. In preliminary experiments, rhFGF-2 treated cells undergo 3 more population doublings than Control cells by the end of first passage, and up to 10 more by the end of fifth passage. The effects of transient rhFGF-2 treatment of the monolayer cells persist when chondrogenesis is induced. Morphometric and biochemical analyses suggest that the increased size of the aggregates is due to increased matrix production by the rhFGF-2 treated hMSCs, and not due to higher number of cells in the aggregates. The mechanism behind this increased synthesis of extracellular matrix has not yet been determined, but the microarray data have provided several candidate genes involved in cell communication and signal transduction (Table). Several of these genes have been reported to participate in the regulation of chondrogenesis and may, therefore, be involved in this enhancement of chondrogenic differentiation induced by exposure to rhFGF-2. Both the mitotic and chondrogenic enhancements could be substantial advantages when using these cells in cartilage repair.

TABLE

List of signal transduction related genes differentially expressed in FGF-treated cells

| Fold-change | Symbol |
|---|---|
| Down-regulated | |
| −19.28 | CLIC3 |
| −9.22 | WISP1 |
| −5.09 | TNFRSF11B |
| −4.57 | MME |
| −4.06 | PDK1 |
| −3.83 | VLDLR |
| −3.31 | PENK |
| −3.25 | INHBA |
| −2.92 | IGFBP3 |
| −2.89 | LIM |
| −2.83 | FN1 |
| −2.79 | EDN1 |
| −2.72 | GADD45B |
| −2.64 | PDGFA |
| −2.59 | CELSR1 |
| −2.58 | JAG1 |
| −2.54 | RGS4 |
| −2.52 | FZD7 |
| −2.47 | IL6 |
| −2.43 | LEPR |
| −2.29 | TGFBR1 |
| −2.29 | FLNB |
| −2.22 | STC2 |
| −2.20 | PTPRF |
| −2.17 | PTPLA |
| −2.10 | CDH2 |
| −2.08 | FGF2 |
| −2.05 | STAT4 |
| −2.05 | LYN |
| −2.02 | SIAH2 |
| −2.01 | TGFB2 |
| −2.00 | TRAF5 |
| Up-regulated | |
| 17.21 | PTPN22 |
| 10.38 | CXCL6 |
| 9.99 | DUSP4 |

TABLE-continued

List of signal transduction related genes
differentially expressed in FGF-treated cells

| Fold-change | Symbol |
|---|---|
| 8.75 | HTR2B |
| 7.44 | HLA-DRB3 |
| 7.35 | SRFP1 |
| 6.55 | BMP2 |
| 6.29 | TRHDE |
| 5.55 | DUSP6 |
| 5.01 | EDNRA |
| 4.30 | HGF |
| 4.30 | HLA-DRB4 |
| 4.23 | ARHGEF3 |
| 4.18 | F2RL1 |
| 4.14 | PTGER2 |
| 3.35 | GRB14 |
| 3.31 | BDKRB2 |
| 3.29 | RDGBB |
| 3.09 | HMGA2 |
| 3.07 | GEM |
| 3.05 | NDP |
| 2.83 | SPRY1 |
| 2.60 | IL7 |
| 2.56 | RGS2 |
| 2.56 | PPRGC1 |
| 2.44 | PPKAR2B |
| 2.43 | CCL2 |
| 2.31 | PBEF |
| 2.22 | SPRY2 |
| 2.18 | TGFBR3 |
| 2.16 | NET1 |
| 2.15 | TNFAIP6 |
| 2.07 | TGFBR2 |
| 2.05 | LIFR |
| 2.03 | PTGFR |
| 2.02 | MAP4K4 |

Example 3

A Method to Improve Chondrogenesis by Adult Mesenchymal Stem Cells

Background:

Successful tissue engineering of articular cartilage has the potential to revolutionize the therapy of degenerative joint diseases. This is particularly true of cartilage tissue engineering based on bone marrow-derived mesenchymal stem cells. This approach has the potential to allow the creation of very large amounts of new cartilage tissue for implantation without the need for harvesting healthy articular cartilage from a non-affected area.

A common implementation of cartilage tissue engineering, which we use as well, is to seed a biodegradable carrier scaffold with cells. The carrier scaffold provides the initial structural properties of the construct, and is then gradually replaced by the cellular component and its products. To support and maintain the cells and their functions during this process, nutrients must be provided to the cells, and waste products must be cleared. tissue-engineered constructs in general, and tissue-engineered cartilage in particular, do not have a built in vasculature. Therefore, the transport of these molecules to and from the cells inside the engineered tissue mass must occur by diffusion. Chondrocytes in their natural environment (2-3 mm thick cartilage) survive for decades and product cartilaginous matrix. This suggests that these terminally differentiated cells are adapted to meet their basal metabolic requirements through diffusion. There are at least three sources of problems, which complicate the routine generation of mesenchymal stem cell-based tissue-engineered cartilage implants. This aspect of the invention targets all three of these.

At early time points, the tissue-engineered constructs are populated by mesenchymal stem cells which are not (yet) adapted to survival under these conditions. Limiting factors are the dimensions of the construct itself, and the metabolic requirements of the cells contained therein. Large constructs therefore face mass transfer issues that lead to limited function and viability. In constructs seeded with mesenchymal stem cells and treated with chondrogenic medium in a bioreactor environment, chondrogenesis begins at the construct surface and proceeds in a centripetal fashion resulting in the formation of a shell of differentiated material surrounding a viable, but undifferentiated core. This is not the desired outcome, which would be a uniform construct.

In addition, mesenchymal stem cells are a non-homogeneous cell population with differing chondrogenic potential. In micromass and aggregate (i.e., pellet) cultures, cells, which do not take part in chondrogenesis, are shed from the construct. The size and shape of tissue-engineered constructs, and the assembly methods used do not allow for the cells to self-sort according to chondrogenic potential.

Finally, the ability of mesenchymal stem cells to differentiate into cartilaginous tissue in tissue-engineered constructs differs markedly from preparation to preparation. In contrast, almost all preparations undergo differentiation in micromass or aggregate/pellet culture. This is likely due to the combination of the first two issues.

Method:

In several model systems of chondrogenesis, e.g., micromass and aggregate/pellet culture, the diffusion distances are reduced to the point where mass transport issues become less dominant. In addition, it allows for a sorting process to take place, in which only certain subpopulations of the mesenchymal stem cell preparation take part in the cartilage formation. Under these conditions, the bulk of the mesenchymal stem cells, which take part in the aggregate/pellet formation differentiate to become chondrocytes. However, this results in constructs that are so small as to be useless from a therapeutic standpoint.

Our new method takes advantage of the aggregate/pellet culture approach, where mass transport is not limiting, to drive the cells down the chondrogenic lineage. In addition, cells, which do not take part in chondrogenesis, are selectively excluded during this period.

Briefly, the aggregate/pellet culture approach is as follows: a suspension of mesenchymal stem cells are placed in sterile conical-bottomed polypropylene vessels in cell culture medium with chondrogenic supplements. About 200,000 to 250,000 cells are placed in each vessel, and these are then centrifuged to aggregate/pellet the cells. The resulting aggregate/pellets are then maintained in culture for several days to allow chondrogenesis to begin.

The innovation we are introducing is that, at this point, the cells are released from the aggregate/pellet environment by enzymatic digestion, and are then used to seed large-scale tissue engineering implants.

Results:

Tests of this method are highly encouraging, yielding: markedly enhanced viability throughout the construct, chondrogenic differentiation of cells from mesenchymal stem cell preps that otherwise exhibited poor chondrogenic potential abundance chondroid extracellular matrix production.

Example 4

Modulation of Growth and Differentiation Conditions Enhances Chondrogenesis in Large Tissue-Engineered Constructs Introduction:

Tissue-engineered implants based on bone marrow derived mesenchymal stem cells (MSCs) are a promising approach to articular cartilage repair. Substrate (e.g., nutrients, waste products) mass transport considerations are critical for any tissue-engineered construct, but our constructs initially contain particularly large numbers of metabolically very active cells. As the constructs mature, abundant, diffusion limiting extracellular matrix is produced. Some substrates that are absolutely required for the induction of chondrogenesis in MSCs are of high MW (e.g., TGF-β1-25 kDa) and have small diffusivity ($10^{-7}$ cm$^2$/sec). Constructs frequently exhibit a peripheral cartilaginous shell, with limited cell function at the center, as substrate availability is limited by both diffusion and cellular consumption. These two limiting factors are targets for interventions designed to improve chondrogenesis. In this study, we hypothesized that manipulating the cells before and after assembly into the constructs could reduce the consumption of externally supplied substrates, and thus enhance viability and chondrogenesis.

Materials and Methods:

Constructs:

Control MSCs were isolated, culture expanded for 2 passages in DMEM+10% FBS, and then vacuum-seeded onto 7.3 mm on porous scaffolds. In this case the outcome of our manipulations was tested on a Fidia, Hyaff-11® material (Fidia, Abano Terme, Italy), as the carrier scaffold at a density of $10^8$ cells/ml, as described previously. Other scaffolds can be used as well. The assembled constructs were grown for 3 weeks in a continuous perfusion bioreactor. Baseline chondrogenic medium was DMEM-HG with 1% ITS+Premix™, 100 µM ascorbate-2-phosphate, $10^{-7}$ M dexamethasone and 10 ng/ml TGF-β1. Three experimental treatments, described below, were used, individually or in combination.

Preconditioning in Aggregate Culture:

In this approach, the expanded cells were pre-conditioned in aggregate culture at 2.5×10$^5$ cells per aggregates by enzymatic digestion, and then assembled into the large constructs as described above. Our working hypothesis is that the initial stages of differentiation can be bridged in the aggregate environment (1-2 mm diameter spheres) where substrate diffusion is less limiting.

Growth Factor Pretreatment:

We have tested several growth factor-based modifications to the growth medium. For this study, the medium was supplemented with 10 ng/ml FGF-2 beginning in primary culture. The mechanism underlying the FGF response remains unclear.

Dynamic Modification of the Chondrogenic Medium:

We have modified the composition of the baseline chondrogenic medium by adding or withdrawing components at defined points during the culture process. In this study, we have tapered the dexamethasone concentration to 0 beginning at day 6. The working hypothesis is that dexamethasone withdrawal induces the internal synthesis of BMP-2, a chondrogenic growth factor.

Outcome Assessment:

At the end of 3 weeks in bioreactor culture, the implants were harvested and processed for standard histology and collagen immunohistochemistry. A subset of the samples was tested mechanically to determine bulk material properties of the constructs.

Figure 19:
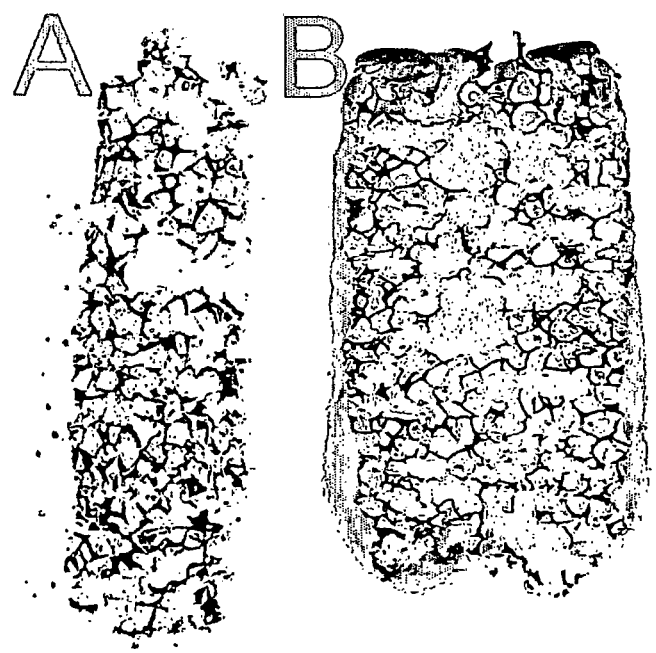
FIG. 19 is a photograph illustrating matched pairs of constructs from the same donor after 3 weeks in culture. (A): cells load immediately after monolayer culture. (B): cells loaded after 3 days in aggregate culture.
Figure 20A:
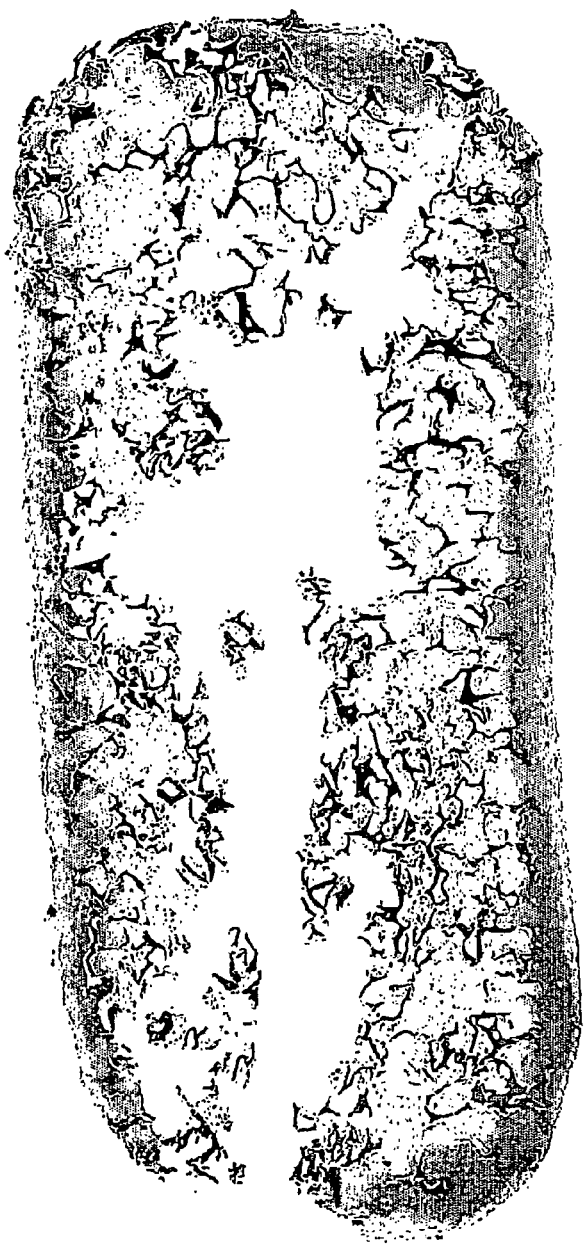
FIGS. 20A and 20B are photographs illustrating 3-week constructs. Top: cell pre-treated with FGF. Bottom: Dexamethasone withdrawn on day 6.
Figure 20B:
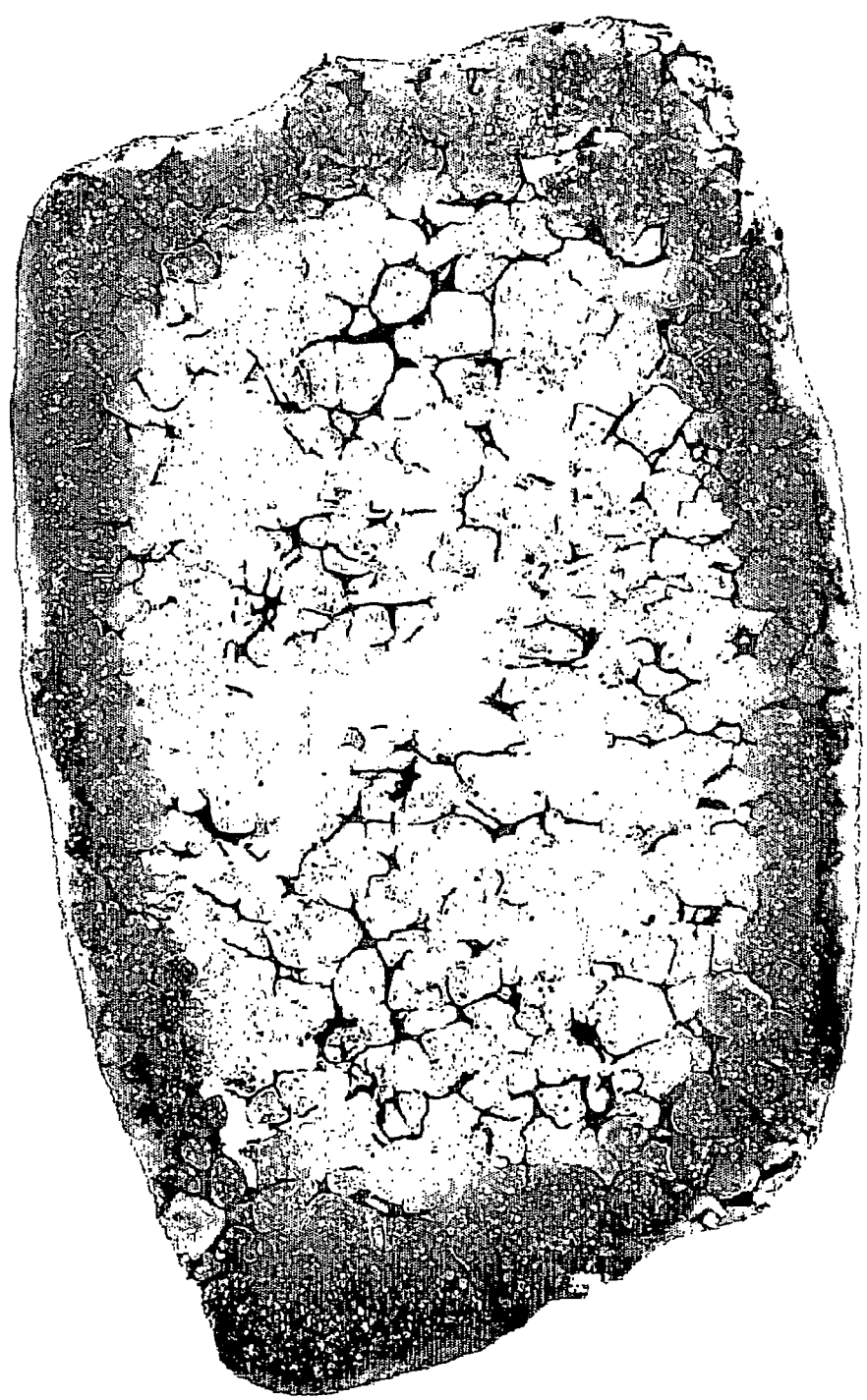
Figure 21:
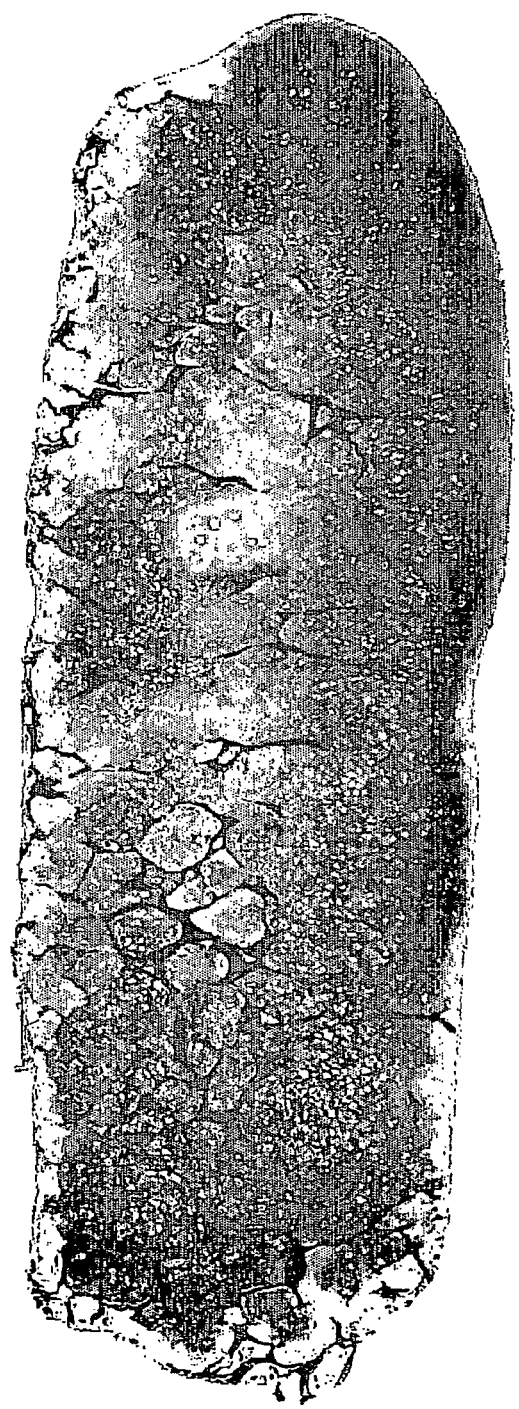
FIG. 21 is a photograph illustrating 3 week construct implementing combined FGF, aggregate pre-treatment, and dexamethasone withdrawal.

Results:

Individually, each of the manipulations described in this study applied to a standardized tissue-engineered construct, improved chondrogenesis to a measurable extent. As shown in FIGS. 19, 20A and 20B, in each case, the thickness of the differentiated layer increased significantly, while cell viability, ECM production and expression of cartilage markers, e.g., type II collagen, GAG increased (not shown). Young's modulus was significantly increased compared to control, and at the light microscopy level, the homogeneity of the synthesized matrix increased as well. Most significantly, the combination of these three treatment protocols has allowed us to achieve full-thickness chondrogenesis (FIG. 21).

Discussion:

The creation of full-thickness cartilage disks based on human mesenchymal stem cells removes a significant obstacle to translating cartilage tissue engineering from the laboratory to the clinic. Future work will include efforts to scale these constructs up beyond their already significant size. Our results suggest that manipulation of the cellular component of the constructs will be a valuable complement to scaffold and bioreactor design optimization in pursuit of these goals.

An additional problem that plagues tissue engineering using human MSCs is a large donor-to-donor variability in chondrogenic potential and biosynthetic activity. Each of the manipulations described in this study greatly reduced, but did not entirely

Example 5

Assessment of Mass Transport Limitations During Cartilage Tissue Engineering Introduction:

Substrate mass transport considerations are very important during the growth of tissue-engineered products in vitro. Due to the lack of an intrinsic convective supply/removal system in tissue-engineered cartilage constructs grown in a bioreactor, the supply/removal of a given substrate to an individual cell within the construct will be limited by diffusion and cellular consumption. In a bioreactor system, mass transfer resistance can occur in one or a combination of regions of the system. External to the construct, mass transfer is dependent on the fluid hydrodynamics in the reactor, and the net consumption/production of the substrate by the tissue. The boundary layer adjacent to the growing tissue is where most of the fluid resistance, as well as mass transfer resistance external to the tissue, resides. Finally, in the implant itself, consumption/production of the substrate dominates. Mass transfer is primarily due to passive diffusion, and a progressive increase in mass transfer resistance is expected as porosity decreases because of matrix production by the cells.

Figure 24:
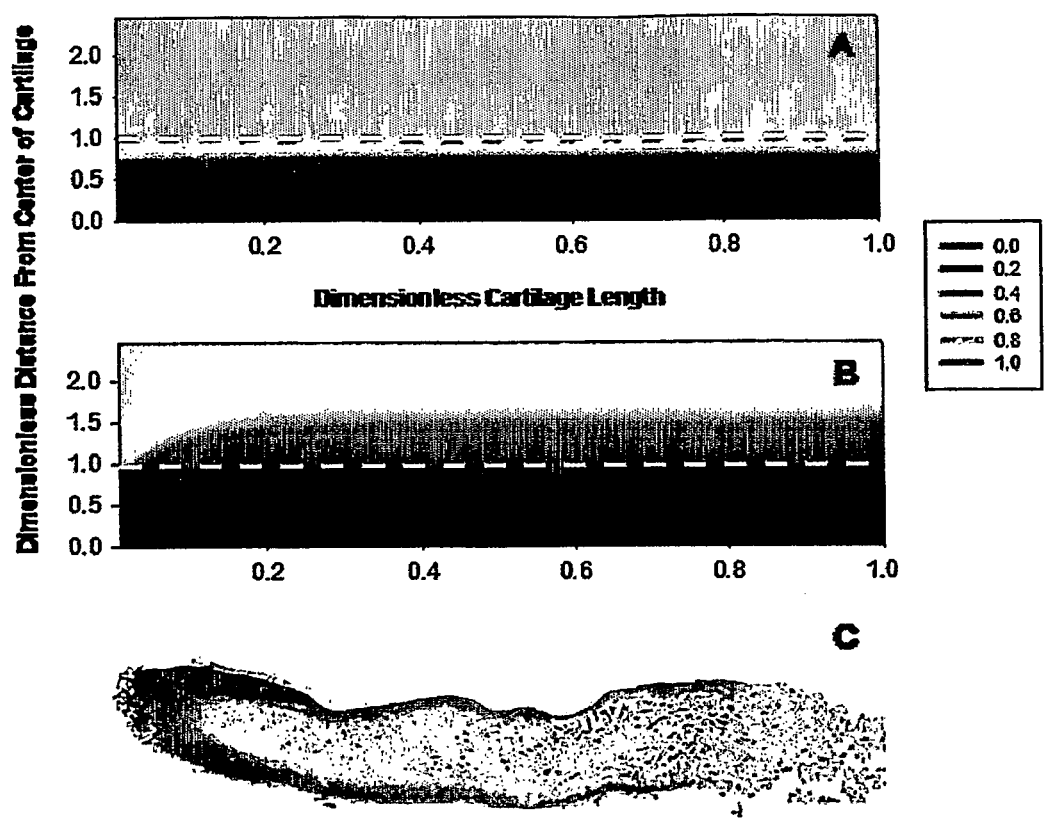
FIG. 24 are photographs illustrating color contours representing fraction of atmospheric $O_2$.

In mesenchymal stem cells (MSC)-based tissue-engineered cartilage, some of the substrates required to induce chondrogenic differentiation are of higher molecular weight (e.g. TGF-β1, 25 kDa), and have small diffusivities ($10^{-7}$ cm$^2$/sec). The constructs initially contain metabolically active cells at very high density and, as the construct matures, abundant extracellular matrix (ECM) is produced. One would therefore predict that the penetration of substrates into the construct would be impeded by the molecular weight of the substrate but also by dynamic variables like the degree of maturity of the ECM and consumption rates by the cells. This hypothesis can explain the formation of a cartilaginous shell at the periphery of the construct (FIG. 24), with limited cell function at the center. The purpose of this study was to test this hypothesis by measuring mass transfer limitations of probe molecules within the tissue-engineered construct as a function of its maturation state.

Methods:

Constructs:

Human bone marrow derived MSCs were isolated, culture expanded, and vacuum seeded onto 7×3 mm hyaluronan-based scaffolds (Hyaff-11®, Fidia Advanced Biopolymers, Abano Terme, Italy), as described previously. The assembled constructs were grown for up to 3 weeks in a continuous perfusion bioreactor with highly $O_2$ permeable walls, in a defined chondrogenic medium (DMEM-HG supplemented with 1% ITS+Premix™, 100 μM ascorbate-2-phosphate, $10^{-7}$ M dexamethasone and 10 ng/ml TGF-β1).

Figure 22A:
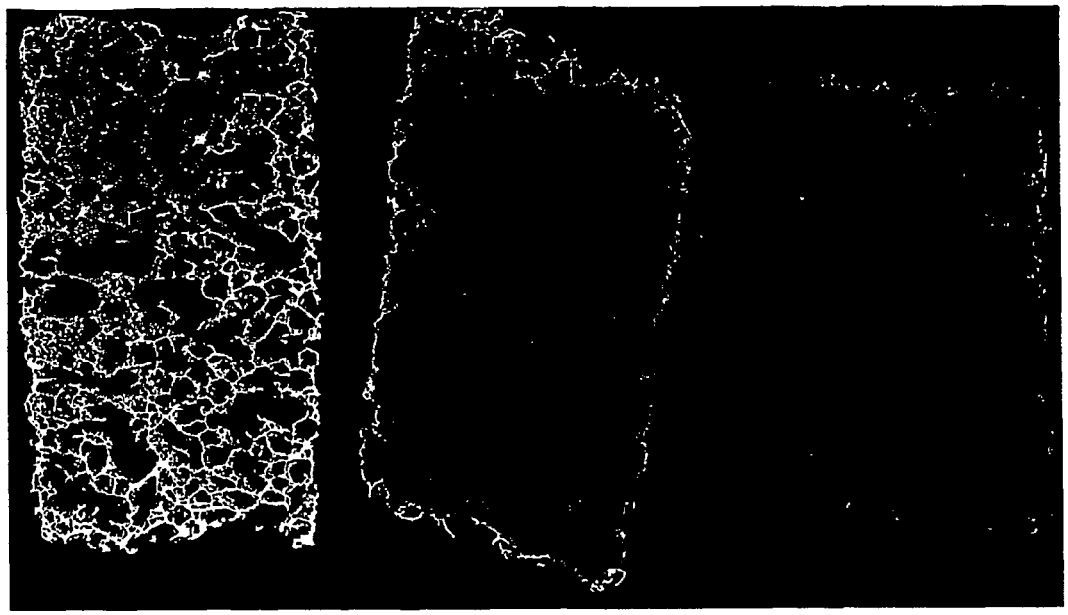
FIGS. 22A and 22B are photographs illustrating constructs labeled with 3, 10 and 70 kDa dextrans (L to R) at days 0 and 7. Fluorescent label shows as white.
Figure 22B:
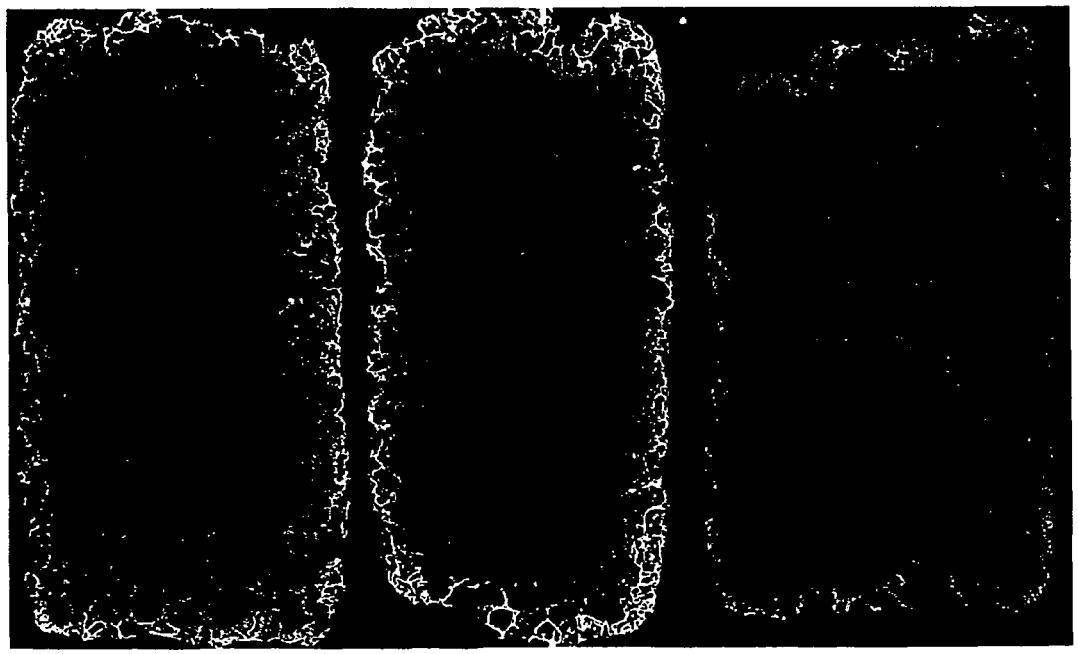
Figure 23:
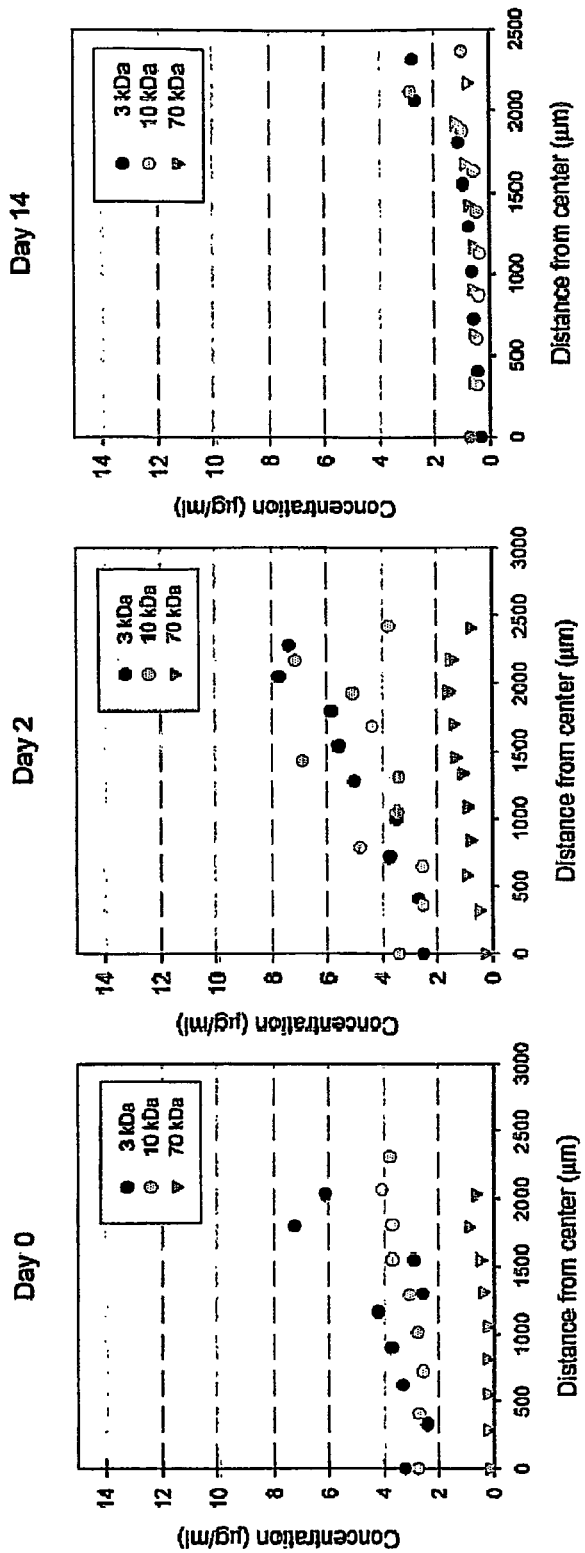
FIG. 23 is a plot illustrating the depth of penetration of each probe as function of MW.

Diffusion Measurements:

To evaluate mass transport limitations of large molecules (e.g., TGF-β), tissue-engineered cartilage constructs were pulsed for 18 hours with fluorescently tagged dextran probes (Molecular Probes, Eugene, Oreg.) of 3, 10, or 70 kDa molecular weight after 0 to 21 days in bioreactor culture. The probes were then cross-linked in situ using formalin, and paraffin sections were obtained. Composite digital images of the sections were used to obtain the local concentrations of the tracers using custom-written image analysis routines (FIGS. 22A and 22B). A numerical model of diffusion into the constructs was developed.

Mass Transport Modeling:

To evaluate mass transport limitations of small molecules (e.g., $O_2$), we developed a convection-diffusion model of mass transport in the reactor system with Michaelis-Menten consumption kinetics occurring in the construct. By using published consumption rates for the cells, the known physical and geometric characteristics of the bioreactor/construct system, and numerical methods, the model was solved to obtain oxygen concentration profiles for a variety of conditions such as the presence and the absence of an internal mixing system.

Results:

In FIGS. 22A and 22B, composition fluorescent micrographs illustrate the diffusion of fluorescent dextran probes into the constructs at several time points after the initiation of chondrogenic differentiation. Examples of the quantitative evaluation are shown in FIG. 27. As hypothesized, the depth of penetration of each probe decreased as a function of the MW of the probe and of the maturity of the construct.

Internal mixing of the bioreactor content at 8 ml/min has a profound effect on the $O_2$ tension in the constructs. Steady-state $O_2$ concentration contours modeled in the bioreactor with (A) and without (B) internal mixing are shown in FIG. 28. The dashed line represents the interface between the cartilage and the medium. Under unmixed conditions, only the very surface of the construct is an $O_2$ tension of 0.2× atmospheric or better, with the center of the construct predicted to be nearly anoxic. (C) Partially differentiated construct grown under condition (B), showing the cartilaginous shell. The mixed model predicts that at 8 ml/min the bulk of the volume of the implant would be above 0.2× atmospheric $O_2$. This is nearly 2× higher than measured $O_2$ tensions in native cartilage samples.

Discussion:

These results suggest a central limiting role for substrate mass transport in the generation of large-scale cartilage implants. The results further support the hypothesis that both the MW of the substrate and the time elapsed since the beginning of chondrogenic differentiation conspire to limit the diffusion of nutrients into the constructs.

Engineering approaches can improve mass transport across each region of the bioreactor/implant system; these include content mixing, changing the medium replenishment rates, and improving the hydrodynamics of the chamber to minimize boundary layer formation. The results from this study will be used to explore engineering solutions to the problem of shell formation, and to assess the countermeasures taken.

Example 6

Figure 25A:
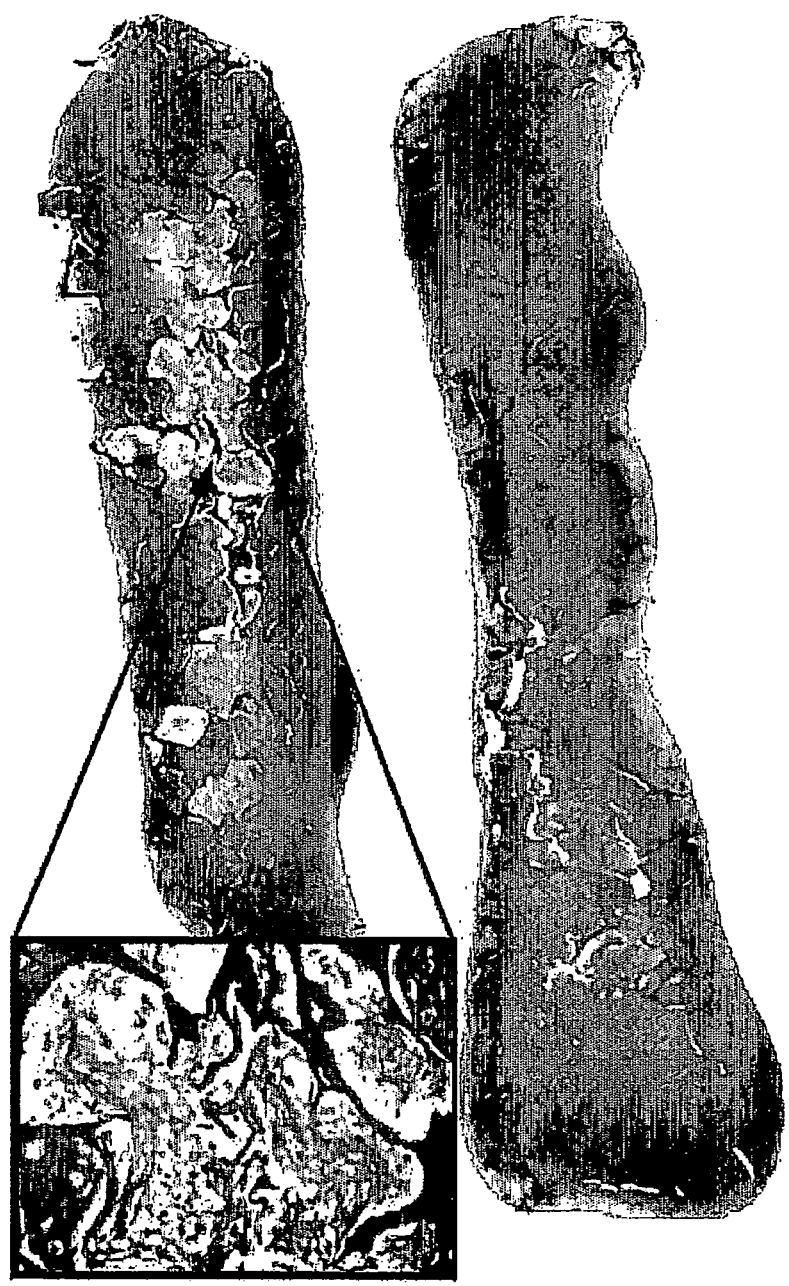
FIG. 25 illustrates constructs assembled from cells preconditioned in aggregate culture for 3 (A) or 5 (B) days prior to assembly.
Figure 25B:
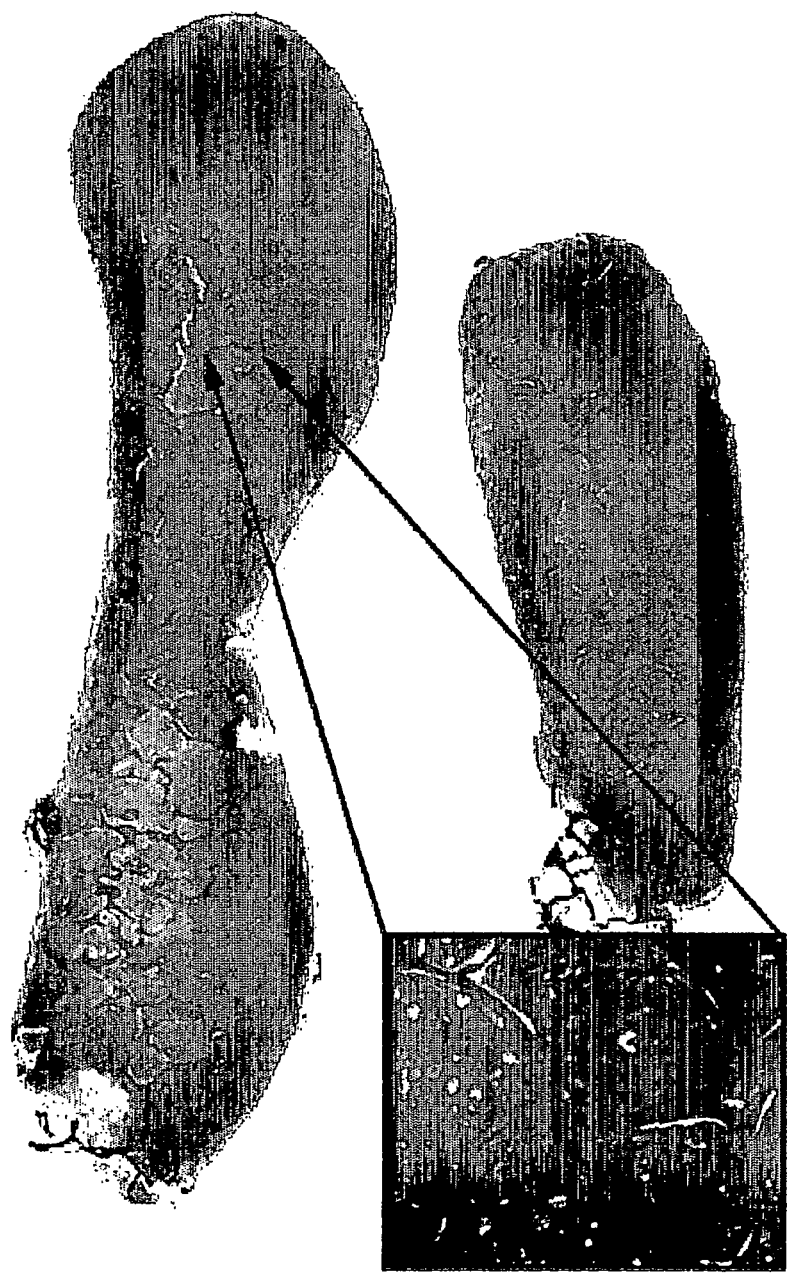

Cell Preconditioning Experiments:

Cells were transiently cultured in aggregate culture, then released, and seeded onto the scaffolds. All aggregate culture modes resulted in an improvement in cell viability and differentiation at the center of the constructs. Evaluation of aggregate culture times of 3, 5, and 7 days, followed by enzymatic release of the cells from the aggregates and assembly into the final constructs suggests that maintaining the cells in aggregate culture for 5 days (FIG. 25A) yields superior results to the 3 days (FIG. 25B) proposed earlier. This is in terms of implant viability, of the amount and "quality" of the synthesized matrix, and of the mechanical properties of the constructs (e.g. 30-50% increase in Young's modulus in "5 day aggregate" vs. "3 day aggregate" constructs). For example, the lighter areas in 3 day constructs (panel A, inset) although clearly viable are filled with a much less dense and organized chondroid matrix than equivalent areas in the 5 day constructs (panel B, inset). Our working hypothesis is that the pre-differentiation in aggregate culture lowers the metabolic requirements of the cells, thus pre-adapting them to the less favorable mass transport conditions in the larger constructs. Although the data are not yet conclusive, it is not clear that extending aggregate dwell time to 7 days results in further improvement (not shown). Taken together, these results, although preliminary, suggest that this preconditioning approach will be extremely useful for MSC-based cartilage tissue engineering.

What has been described above includes examples and implementations of the present invention. Because it is not possible to describe every conceivable combination of components, circuitry or methodologies for purposes of describing the present invention, one of ordinary skill in the art will recognize that many further combinations and permutations of the present invention are possible. Accordingly; the present invention is intended to embrace all such alterations, modifications and variations that fall within the spirit and scope of the appended claims.

Having described the invention, the following is claimed:

1. A bioreactor comprising:
   a housing defining a first chamber that contains a first liquid medium, the housing including an inlet port and an outlet port for fluid flow of the liquid medium through the first chamber, the liquid medium including at least one of a growth or culture medium for growing or culturing cells in the first chamber;
   at least one gas permeable membrane defining at least a portion of the housing, the membrane allowing gas flow through the housing into the first chamber; and
   a hydrostatic loading module that transmits hydrostatic pressure through the membrane to the first liquid medium contained in the first chamber.

2. The bioreactor of claim 1, the hydrostatic loading module transmitting the pressure by a static second liquid medium.

3. The bioreactor of claim 1, the hydrostatic loading module being attached to the housing and forming a second chamber with the housing, the second chamber containing a second liquid medium and being separated from the first chamber by the gas permeable membrane.

4. The bioreactor of claim 3, the hydrostatic loading module including at least one pump for increasing or decreasing the pressure of the second liquid medium in the second chamber.

5. The bioreactor of claim 3, the hydrostatic loading module being capable of increasing or decreasing the hydrostatic pressure in the first chamber.

6. The bioreactor of claim 4, the hydrostatic loading module further including a pressure sensor for monitoring the pressure in the second chamber.

7. The bioreactor of claim 1, the housing including a frame, the frame including a first surface, a second surface spaced apart and aligned with the first surface, and an opening that extends through the frame from the first surface to the second surface.

8. The bioreactor of claim 7, the housing including a first gas permeable membrane attached to the first surface of the frame and a second gas permeable membrane attached to the second surface of the frame, the first gas permeable membrane, the second gas permeable membrane, and the frame defining the first chamber.

9. The bioreactor of claim 1, the hydrostatic loading module being attached to the housing and including a second chamber and a third chamber, the second chamber and the third chamber containing a second liquid medium and being separated from the first chamber by, respectively, a first gas permeable membrane and a second gas permeable membrane.

10. The bioreactor of claim 1, the at least one gas permeable membrane having sufficient optical transparency to permit visual observation of the first chamber.

11. The bioreactor of claim 10, the at least one gas permeable membrane being resistant to cell attachment.

12. The bioreactor of claim 1, further including a pH sensor, the pH sensor measuring the pH of the first liquid medium entering the first chamber and exiting the first chamber.

13. The bioreactor of claim 1, further including an impeller for circulating the first liquid medium in the first chamber.

14. The bioreactor of claim 1, including a first flow control valve positioned in the inlet port and a second flow control valve positioned in the outlet port, the first flow control valve and the second flow control valve regulating the flow of the first liquid medium through the first chamber.

15. The bioreactor of claim 1, the inlet port and the outlet port being sealed during hydrostatic loading to allow the hydrostatic pressure of the first chamber to be increased without loss of first liquid medium from the first chamber.

16. The bioreactor of claim 3, the second chamber being sealed to pressurize the second liquid medium and thereby transmit hydrostatic pressure through the gas permeable membrane and into the first chamber.

17. A bioreactor comprising:
a housing defining a first chamber, a second chamber, and a first gas permeable membrane separating the first chamber and the second chamber and allowing gas flow between the first chamber and the second chamber, the first chamber containing a first liquid medium and including an inlet port and an outlet port for fluid flow of the first liquid medium through the chamber, the first liquid medium being used to culture or grow cells or tissue in the first chamber, the second chamber containing a second liquid medium and including an inlet and outlet for fluid flow of the second liquid medium through the second chamber; the hydrostatic pressure of the second liquid medium being transmitted through the first gas permeable membrane to affect the hydrostatic pressure of the first liquid medium contained in the first chamber.

18. The bioreactor of claim 17, further including at least one pump for increasing or decreasing the pressure of the second liquid medium in the second chamber.

19. The bioreactor of claim 18, further including a pressure sensor for monitoring the pressure in the second chamber.

20. The bioreactor of claim 17, the housing including a frame, the frame including a first surface, a second surface spaced apart and aligned with the first surface, and an opening that extends through the frame from the first surface to the second surface.

21. The bioreactor of claim 20, the gas permeable membrane being attached to the first surface of the frame, and the housing further including a second gas permeable membrane attached to the second surface of the frame, the first gas permeable membrane, the second gas permeable membrane, and frame defining the first chamber.

22. The bioreactor of claim 21, including a third chamber, the third chamber containing the second liquid medium and being separated from the first chamber by the second gas permeable membrane.

23. The bioreactor of claim 22, the first gas permeable membrane and the second gas permeable membrane having sufficient optical transparency to permit visual observation of the first chamber.

24. The bioreactor of claim 17, the first gas permeable membrane being resistant cell attachment.

25. The bioreactor of claim 17, further including a pH sensor, the pH sensor measuring the pH of the first liquid medium entering the first chamber and exiting the first chamber.

26. The bioreactor of claim 17, further including an impeller for circulating the first liquid medium in the first chamber.

27. The bioreactor of claim 1, the inlet port including a first flow control valve and the outlet port including a second flow control valve, the first flow control valve and the second flow control valve regulating the flow of the first liquid medium through the first chamber.

28. A bioreactor comprising:
a housing defining a first chamber that contains a first liquid medium and a plurality of cells, the housing including an inlet port and an outlet port for fluid flow of the liquid medium through the first chamber, the liquid medium including at least one of a growth or culture medium for growing or culturing the plurality of cells in the first chamber;
at least one gas permeable membrane defining at least a portion of the housing, the membrane allowing gas flow through the housing into the first chamber; and
a hydrostatic loading module for transmitting hydrostatic pressure through the membrane to the first liquid medium and the plurality of cells contained in the first chamber.

29. The bioreactor of claim 28, the plurality of cells contained in the first chamber being seeded on at least one of a scaffold or sponge.

30. The bioreactor of claim 29, the plurality of cells comprising mesenchymal stem cells.

31. The bioreactor of claim 30, the mesenchymal stem cells being treated with a cytokine to promote differentiation into chondrogenic tissue.

32. The bioreactor of claim 30, the mesenchymal stem cells being aggregated prior to being seeded on the scaffold or sponge.

33. The bioreactor of claim 32, the hydrostatic loading module being attached to the housing and forming a second chamber with the housing, the second chamber containing a second liquid medium and being separated from the first chamber by the gas permeable membrane.

34. The bioreactor of claim 28, the hydrostatic loading module being attached to the housing and including a second chamber and a third chamber, the second chamber and the third chamber containing a second liquid medium and being separated from the first chamber by, respectively, a first gas permeable membrane and a second gas permeable membrane.

35. The bioreactor of claim 28, the plurality of cells being suspended in the first liquid medium.

36. The bioreactor of claim 28, the first liquid medium promoting chondrogenesis.

37. A method of preparing chondrogenic tissue construct, the method comprising:
    isolating a plurality of mesenenchymal stem cells from bone marrow;
    expanding the mesenchymal stem cells in a culture medium;
    seeding the expanded mesenchymal stem cells onto a construct;
    growing the seeded construct in a chondrogenic medium; and
    hydrostatically loading the seeded construct while the seeded construct is grown in the chondrogenic medium.

38. The method of claim 37, the seeded construct being grown in the chamber of a bioreactor, the chamber being perfused with the chondrogenic medium, the bioreactor allowing for hydrostatic loading of the seeded construct in the bioreactor chamber, without removing the seeded construct from the chamber.

39. The method of claim 37, the hydrostatic loading being applied cyclically to the seeded construct.

40. The method of claim 37, the mesenchymal stem cells being treated with a cytokine to promote differentiation to chondrocytes.

41. The method of claim 40, the cytokine comprising fibroblast growth factor 2 (rhFGF-2).

42. The method of claim 37, further comprising,
    providing a suspension of mesenchymal stem cells in a culture medium contained in a sterile vessel;
    aggregating the mesenchymal stem cells in the vessel,
    maintaining the aggregated mesenchymal stem cells in culture for a duration of time sufficient to allow chondrogenesis to begin;
    releasing the mesenchymal stem cells from aggregate; and
    seeding the construct with the released cells.

43. The method of claim 37, chondrogenic medium containing a first concentration of dexamethasone; and
    reducing the concentration of dexamethasone in the chondrogenic medium during growing to a second concentration substantially less than the first concentration, the second concentration of the dexamethasone being effective to induce the expression of BMP-2 in the cells.

44. The bioreactor of claim 1, the at least one gas permeable membrane comprising two membranes having substantially identical gas permeability and being positioned on opposite sides of the first chamber.

* * * * *